(12) United States Patent
Lavrovsky et al.

(10) Patent No.: US 11,155,600 B2
(45) Date of Patent: Oct. 26, 2021

(54) HUMAN IL1-R1 DERIVED INHIBITOR OF IL-1β

(71) Applicant: R-Pharm Overseas, Inc., San Diego, CA (US)

(72) Inventors: Yan Lavrovsky, Del Mar, CA (US); Ting Xu, Needham, MA (US); Elena Batienko, San Diego, CA (US); Anna Krotkova, Moscow (RU); Vasily Ignatiev, Moscow (RU); Mikhail Samsonov, Moscow (RU); Alexey Repik, Moscow (RU)

(*) Notice: Subject to any disclaimer, the term of this patent is extended or adjusted under 35 U.S.C. 154(b) by 0 days.

(21) Appl. No.: 15/129,412

(22) PCT Filed: Mar. 24, 2014

(86) PCT No.: PCT/US2014/031622
§ 371 (c)(1),
(2) Date: Sep. 26, 2016

(87) PCT Pub. No.: WO2015/147789
PCT Pub. Date: Oct. 1, 2015

(65) Prior Publication Data
US 2017/0226185 A1    Aug. 10, 2017

(51) Int. Cl.
*C07K 14/715*    (2006.01)
*A61K 38/17*    (2006.01)
*A61K 38/00*    (2006.01)

(52) U.S. Cl.
CPC ...... *C07K 14/7155* (2013.01); *A61K 38/1793* (2013.01); *C07K 14/715* (2013.01); *A61K 38/00* (2013.01); *C07K 2319/30* (2013.01)

(58) Field of Classification Search
CPC . C07K 2319/30; C07K 14/7155; A61K 38/00
See application file for complete search history.

(56) References Cited

U.S. PATENT DOCUMENTS 6,927,044 B2 *  8/2005  Stahl ................. C07H 21/04
                                                 435/69.7

* cited by examiner

*Primary Examiner* — Ruixiang Li
(74) *Attorney, Agent, or Firm* — SciTech Legal, P.C.; Yakov M. Korkhin, Esq.

(57) ABSTRACT

A therapeutic composition is described that can be used for treating or prevention of diseases association with modulation of activity of human IL-1β. In certain aspects, the disclosed invention is based, on engineering of a heterodimeric protein assembly that is capable of binding to human IL-1β and attenuating its function. The heterodimeric protein assembly comprises extracellular portions of human IL1-R1 and of human IL-1RAcP, or their functional fragments. Each, the IL1-R1 portion and the IL-1RAcP portion, is fused to a distinct mutant of Fc portion of the human Ig Gamma-1. The two distinct Fc mutants in the heterodimeric protein assembly are engineered as to favor the heteromeric dimer formation between the two Fc mutants over any homomeric assembly. The therapeutic composition has been formulated for administration into humans and animals.

2 Claims, 9 Drawing Sheets

Specification includes a Sequence Listing.

HUMAN IL1-R1 DERIVED INHIBITOR OF IL-1β

CROSS-REFERENCE TO RELATED APPLICATIONS

This application is a US National Stage entry of International Application No. PCT/US14/31622, filed on Mar. 24, 2014. The entire content of the aforementioned applications is incorporated herein by reference.

FIELD OF THE INVENTION

Generally, the invention relates to the field of biological pharmaceuticals as well as their use in conditions associated with inflammatory disorders (e.g rheumatoid arthritis, Crohn's disease, etc.), diabetes, cardiovascular disease and gout. More specifically, the invention relates to a heterodimeric IL-1R1/IL-1RAcP-derived composition that is capable of inhibiting IL-1β cytokine.

BACKGROUND

The interleukin-1 (IL-1) family of cytokines comprises 11 proteins (IL-1F1 to IL-1F11) encoded by 11 distinct genes in humans and mice. IL-1-type cytokines are major mediators of innate immune reactions, and blockade of the founding members IL-1 or IL-1β by the interleukin-1 receptor antagonist (IL-1RA) has demonstrated a central role of IL-1 in a number of human autoinflammatory diseases. IL-1 or IL-1β rapidly increase messenger RNA expression of hundreds of genes in multiple different cell types. The potent proinflammatory activities of IL-1 and IL-1β are restricted at three major levels: (i) synthesis and release, (ii) membrane receptors, and (iii) intracellular signal transduction. This pathway summarizes extracellular and intracellular signaling of IL-1 or IL-1β, including positive- and negative-feedback mechanisms that amplify or terminate the IL-1 response. In response to ligand binding of the receptor, a complex sequence of combinatorial phosphorylation and ubiquitination events results in activation of nuclear factor kappa-B signaling and the JNK and p38 mitogen-activated protein kinase pathways, which, cooperatively, induce the expression of canonical IL-1 target genes (such as IL-6, IL-8, MCP-1, COX-2, IB, IL-1, IL-1β, MKP-1) by transcriptional and posttranscriptional mechanisms. Of note, most intracellular components that participate in the cellular response to IL-1 also mediate responses to other cytokines (IL-18 and IL-33), Toll-like-receptors (TLRs), and many forms of cytotoxic stresses (see Weber A, et al., Sci Signal., 2010 Jan. 19; 3(105), the entire teachings of which are incorporated by reference herein).

IL-1 and IL-1β independently bind the type I IL-1 receptor (IL-1R1), which is ubiquitously expressed. A third specific ligand, the IL-1 receptor antagonist (IL-1RA), binds the IL-1RI with similar specificity and affinity but does not activate the receptor and trigger downstream signaling. The IL-1 receptor accessory protein (IL-1RAcP) serves as a co-receptor that is required for signal transduction of IL-1/IL-1RI complexes, and this co-receptor is also necessary for activation of IL-1R1 by other IL-1 family members, in particular IL-18 and IL-33. The type II IL-1 receptor (IL-1R2) binds IL-1 and IL-1β but lacks a signaling-competent cytosolic part and thus serves as a decoy receptor. The IL-1RA, the plasma membrane-anchored IL-1R2, and the naturally occurring "shed" domains of each of the extracellular IL-1 receptor chains (termed sIL-1RI, sIL-1RII, and sIL-1RAcP, where "s" stands for soluble) provide inducible negative regulators of IL-1 signaling in the extracellular space whose abundance, which is regulated by a combination of increased transcription and controlled release, can limit or terminate IL-1 effects.

The initial step in IL-1 signal transduction is a ligand-induced conformational change in the first extracellular domain of the IL-1RI that facilitates recruitment of IL-1RacP. Through conserved cytosolic regions called Toll- and IL-1R-like (TIR) domains, the trimeric complex rapidly assembles two intracellular signaling proteins, myeloid differentiation primary response gene 88 (MYD88) and interleukin-1 receptor-activated protein kinase (IRAK) 4. Mice lacking MYD88 or IRAK4 show severe defects in IL-1 signaling. Similarly, humans with mutations in the IRAK4 gene have defects in IL-1RI and Toll-like receptor (TLR) signaling. IL-1, IL-1RI, IL-RAcP, MYD88, and IRAK4 form a stable IL-1-induced first signaling module. This is paralleled by the (auto)phosphorylation of IRAK4, which subsequently phosphorylates IRAK1 and IRAK2, and then this is followed by the recruitment and oligomerization of tumor necrosis factor-associated factor (TRAF) 6. IRAK1 and 2 function as both adaptors and protein kinases to transmit downstream signals. Complexes of IRAK1, IRAK2, and TRAF6 dissociate from the initial receptor complex, and cells lacking these proteins have impaired activation of the transcription factors nuclear factor kappa-B (NF-kappa-B) and activator protein 1 (AP-1).

Overproduction of IL-1 is the cause of many inflammatory disorders. For example, IL-1 has been linked to the pathology of diabetes, cardiovascular disease, gout, certain types of arthritis (e.g. rheumatoid arthritis (RA)), as well as a number of less prevalent autoimmune diseases, such as familial Mediterranean fever (FMF), Behcet disease, etc. (Ozen S, Bilginer Y. "A clinical guide to autoinflammatory diseases: familial Mediterranean fever and next-of-kin", Nat. Rev. Rheumatol. 2014 March; 10(3): 135-47).

Rilonacept is an IL-1 antagonist which includes an IL-1-specific fusion protein which comprises an IL-1 binding portion of the extracellular domain of human IL1-RAcP, an IL-1 binding portion of the extracellular domain of human IL-1RI, and a multimerizing component. This IL-1-specific fusion protein is described in U.S. Pat. No. 6,472,179, U.S. patent publication No. 2003/0143697, published 31 Jul. 2003, U.S. Pat. No. 7,361,350, and U.S. patent publication No. 2005/0197293, published 8 Sep. 2005 (all of which are incorporated by reference herein in their entirety). Rilonacept under the trade name ARCALYST was approved by U.S. Food and Drug Administration (FDA) for the treatment of Cryopyrin-Associated Periodic Syndromes (CAPS), including Familial Cold Auto-inflammatory Syndrome (FCAS) and Muckle-Wells Syndrome (MWS) in adults and children 12 and older. Further clinical trials of rilonacept are currently under way, i.e. for gout.

SUMMARY OF THE INVENTION

This summary is provided to introduce a selection of concepts in a simplified form that are further described below in the Detailed Description. This summary is not intended to identify key features or essential features of the claimed subject matter, nor is it intended to be used as an aid in determining the scope of the claimed subject matter.

In certain aspects, the present invention provides for a heterodimeric protein composition capable of binding human IL-1β (GenBank: AAH08678.1). The protein composition comprises a first polypeptide which includes a first amino acid sequence which contains amino acids 18 through 333 of human IL1-R1 (GenBank: AAM88423.1), and a second amino acid sequence which contains a first mutant of a Fc portion of human immunoglobulin gamma-1 Fc (GenBank: J00228.1). The protein composition also comprises a second polypeptide which includes another first amino acid sequence containing amino acids 21 through 358 of human IL1-RAcP (GenBank: BAA25421.1), and another second amino acid sequence which contains a second mutant of the Fc portion of human immunoglobulin gamma-1 Fc. In the protein composition, the first and second mutants are selected as to favor heterodimeric assembly between the first and second mutants over any homodimeric assembly. The protein composition may be capable of exhibiting human IL-1β/IL-1F2 binding activity with a Kd values of no more than about $10^{-11}$M. The first polypeptide of the protein composition may contain amino acid sequence of SEQ ID NO. 1, while the second polypeptide may contain amino acid sequence of SEQ ID NO. 2.

In certain aspects, the present invention provides for a therapeutic composition. The therapeutic composition comprises a heterodimeric protein composition capable of binding human IL-1β. The protein composition comprises a first polypeptide which includes a first amino acid sequence which contains amino acids 18 through 333 of human IL1-R1, and a second amino acid sequence which contains a first mutant of the Fc portion of human immunoglobulin gamma-1 Fc. The protein composition also comprises a second polypeptide which includes another first amino acid sequence containing amino acids 21 through 358 of human IL1-RAcP, and another second amino acid sequence which contains a second mutant of the Fc portion of human immunoglobulin gamma-1 Fc. In the protein composition, the first and second mutants are selected as to favor heterodimeric assembly between the first and second mutants over any homodimeric assembly. The protein composition may be capable of exhibiting human IL-1β/IL-1F2 binding activity with a Kd values of no more than about $10^{-11}$M. The therapeutic composition may exhibit a half-life of the heterodimeric protein composition in systemic circulation in mice after a subcutaneous administration at a dose of 5 mg/kg of at least about 97 hours, as assayed by human Fc ELISA. The therapeutic composition may exhibit a half-life of the heterodimeric protein composition in systemic circulation in Cynomolgus monkeys after a subcutaneous administration at a dose of 10 mg/kg of at least about 3 days, as assayed by human Fc ELISA. The therapeutic composition may comprise a heterodimeric protein comprised of a first polypeptide containing amino acid sequence of SEQ ID NO. 1 and a second polypeptide containing amino acid sequence of SEQ ID NO. 2. The therapeutic composition may also contain about 6% (m/v) sucrose, about 3% (m/v) polyethylene glycol with an average molecular weight of about 3350 Da, about 50 mM sodium chloride, and about 20 mM L-Histidine pH 6.5.

In certain aspects, the present invention provides for use of a substance for manufacture of a medicament for the treatment or prevention of a disease associated with modulation of activity of human IL-1β. The substance comprises a heterodimeric protein comprised of a first polypeptide containing amino acid sequence of SEQ ID NO. 1 and a second polypeptide containing amino acid sequence of SEQ ID NO. 2. The disease associated with modulation of activity of human IL-1β may be an arthritis, a gout, a rheumatoid arthritis, a Cryopyrin-Associated Periodic Syndromes (CAPS), a scleroderma, a diabetes, a atherosclerosis, a dry eye disease, an ocular allergy, an uveitis, a familial Mediterranean fever (FMF), or a Behcet disease.

In certain aspects, the present invention provides for a method of treating or preventing a disease or condition associated with modulation of activity of human IL-1β. The method comprising administering to a patient in need for treating or preventing a disease associated with modulation of activity of human IL-1β a therapeutically effective amount of a pharmaceutical composition. The pharmaceutical composition comprising a heterodimeric protein comprised of a first polypeptide containing amino acid sequence of SEQ ID NO. 1 and a second polypeptide containing amino acid sequence of SEQ ID NO. 2. The disease associated with modulation of activity of human IL-1β may be an arthritis, a gout, a rheumatoid arthritis, a Cryopyrin-Associated Periodic Syndromes (CAPS), a scleroderma, a diabetes, a atherosclerosis, a dry eye disease, an ocular allergy, an uveitis, a familial Mediterranean fever (FMF), or a Behcet disease.

BRIEF DESCRIPTION OF THE DRAWINGS

The following drawings and descriptions are provided to aid in the understanding of the invention.

DETAILED DESCRIPTION OF THE INVENTION

Figure 1:
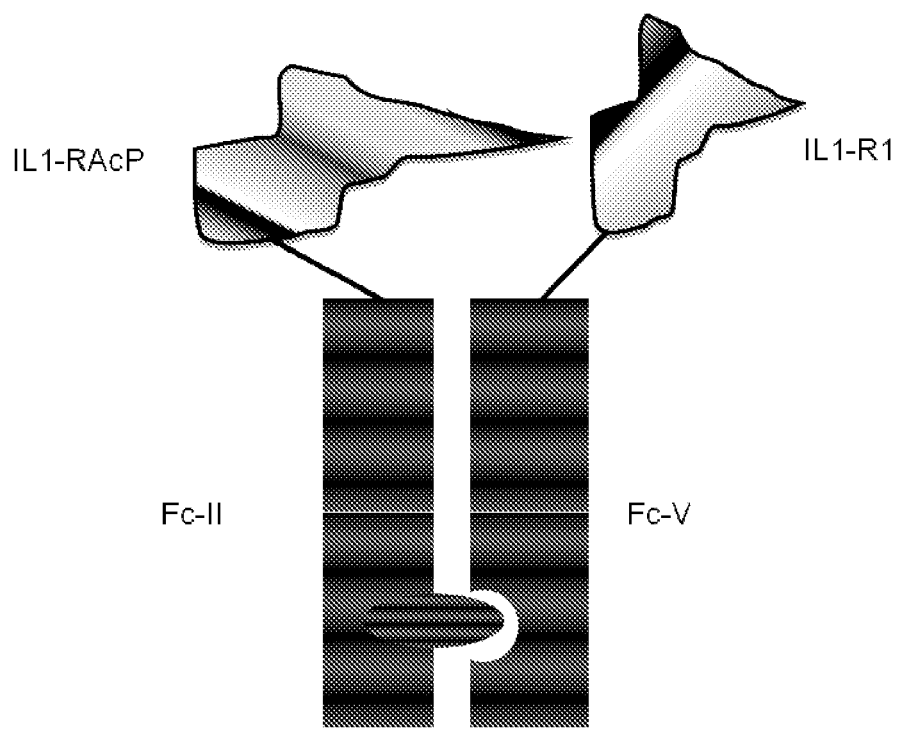
FIG. 1 illustratively shows a heterodimeric protein assembly of the present teachings comprising an extracellular portion of IL1-R1 fused with an IgG-Fc domain (Fc-II) via a flexible linker and an extracellular portion of IL1-RAcP fused with another IgG-Fc domain (Fc-V) via another flexible linker.

The teachings disclosed herein are based, in part, upon engineering of a heterodimeric protein assembly that is capable of binding to human IL-1β and attenuating its function. The heterodimeric protein assembly of the present teachings comprises an extracellular portions of IL1-R1 (GenBank: AAM88423.1) and of IL-1RAcP (GenBank: BAA25421.1), or functional fragments thereof. Each, the IL1-R1 portion and the IL-1RAcP portion, is fused to a distinct mutant of Fc portion of the human Ig Gamma-1 (GenBank: J00228.1). The two distinct Fc mutants in the heterodimeric protein assembly are engineered as to favor the heteromeric dimer formation between the two Fc mutants over any homomeric assembly. To enable recombinant production of the heterodimeric protein assembly of the present teachings, a DNA expression vector has been constructed for overproducing the heterodimeric protein assembly in a heterologous protein expression system, and mammalian cells have been prepared stably expressing the heterodimeric protein assembly to a high expression level. A protein purification procedure has been devised allowing obtaining a physiologically relevant substantially pure preparation of the heterodimeric protein assembly of the present teachings. Thus purified protein molecule demonstrates a high degree of specific activity in an in vitro Enzyme-Linked Immunosorbent Assay (ELISA) using human IL-1β (GenBank: AAH08678.1). Unexpectedly, the protein molecule exhibits an acceptable pharmacokinetics profile upon subcutaneous animal administration, while not resulting in any body weight loss or adverse clinical events. Design, preparation and preliminary characterization of composition of matter of the present teachings are disclosed, in part, in an International Patent Application Publication No. WO/2014/035361, published on Mar. 6, 2014, and International Patent Application Serial No. PCT/US/2013/026349, filed on Feb. 15, 2013, both of which are incorporated herein by reference in their entirety.

The terms used in this specification generally have their ordinary meanings in the art, within the context of this invention and in the specific context where each term is used. Certain terms are discussed below or elsewhere in the specification, to provide additional guidance to the practitioner in describing the compositions and methods of the invention and how to make and use them. The scope or meaning of any use of a term will be apparent from the specific context in which the term is used. "About" and "approximately" shall generally mean an acceptable degree of error for the quantity measured given the nature or precision of the measurements. Typically, exemplary degrees of error are within 20 percent (%), preferably within 10%, and more preferably within 5% of a given value or range of values. Alternatively, and particularly in biological systems, the terms "about" and "approximately" may mean values that are within an order of magnitude, preferably within 5-fold and more preferably within 2-fold of a given value. Numerical quantities given herein are approximate unless stated otherwise, meaning that the term "about" or "approximately" can be inferred when not expressly stated.

The methods of the invention may include steps of comparing sequences to each other, including wild-type sequence to one or more mutants (sequence variants). Such comparisons typically comprise alignments of polymer sequences, e.g., using sequence alignment programs and/or algorithms that are well known in the art (for example, BLAST, FASTA and MEGALIGN, to name a few). The skilled artisan can readily appreciate that, in such alignments, where a mutation contains a residue insertion or deletion, the sequence alignment will introduce a "gap" (typically represented by a dash, or "Λ") in the polymer sequence not containing the inserted or deleted residue.

The methods of the invention may include statistical calculations, e.g. determination of IC50 or EC50 values, etc. The skilled artisan can readily appreciate that such can be performed using a variety of commercially available software, e.g. PRISM (GraphPad Software Inc, La Jolla, Calif., USA) or similar.

"Homologous," in all its grammatical forms and spelling variations, refers to the relationship between two proteins that possess a "common evolutionary origin," including proteins from superfamilies in the same species of organism, as well as homologous proteins from different species of organism. Such proteins (and their encoding nucleic acids) have sequence homology, as reflected by their sequence similarity, whether in terms of percent identity or by the presence of specific residues or motifs and conserved positions. However, in common usage and in the instant application, the term "homologous," when modified with an adverb such as "highly," may refer to sequence similarity and may or may not relate to a common evolutionary origin.

The term "sequence similarity," in all its grammatical forms, refers to the degree of identity or correspondence between nucleic acid or amino acid sequences that may or may not share a common evolutionary origin.

The terms "protein" and "polypeptide" are used interchangeably. The polypeptides described herein may be comprised of more than one contiguous amino acid chain, thus forming dimers or other oligomeric formations. In general, the polypeptides of the present teachings for use in mammals are expressed in mammalian cells that allow for proper post-translational modifications, such as CHO or HEK293 cell lines, although other mammalian expression cell lines are expected to be useful as well. It is therefore anticipated that the polypeptides of the present teachings may be post-translationally modified without substantially effecting its biological function.

In certain aspects, functional variants of the heterodimeric protein assemblies of the present teachings include fusion proteins having at least a biologically active portion of the human IL1-R1 or IL-1RAcP or a functional fragment thereof, and one or more fusion domains. Well known examples of such fusion domains include, but are not limited to, polyhistidine, Glu-Glu, glutathione S transferase (GST), thioredoxin, protein A, protein G, an immunoglobulin heavy chain constant region (e.g., an Fc), maltose binding protein (MBP), or human serum albumin. A fusion domain may be selected so as to confer a desired property. For example, the IL1-R1 or IL-1RAcP polypeptide portions may be fused with a domain that stabilizes the IL1-R1 or IL-1RAcP polypeptides in vivo (a "stabilizer" domain), optionally via a suitable peptide linker. The term "stabilizing" means anything that increases the half life of a polypeptide in systemic circulation, regardless of whether this is because of decreased destruction, decreased clearance, or other pharmacokinetic effect. Fusions with the Fc portion of an immunoglobulin are known to confer desirable pharmacokinetic properties on certain proteins. Likewise, fusions to human serum albumin can confer desirable properties. Other types of fusion domains that may be selected include multimerizing (e.g., dimerizing, tetramerizing) domains and functional domains that confer an additional biological function, e.g. promoting accumulation at the targeted site of action in vivo.

In certain aspects, the heterodimeric protein assemblies of the present teachings comprise an extracellular portion of IL1-R1, or a functional fragment thereof, fused with a IgG-Fc domain, and an extracellular portion IL-1RAcP, or a functional fragment thereof, fused with another IgG-Fc domain. The IgG-Fc domain and the another IgG-Fc domain are chosen as to favor a heterodimeric protein assembly over any homodimeric protein assembly. The extracellular portion of IL1-R1 may be fused with the IgG-Fc domain via a flexible linker, while IL-1RAcP, or a functional fragment thereof, may be fused with the another IgG-Fc domain via the flexible linker of the same amino acid sequence or via another flexible linker.

In an example embodiment, illustratively shown in FIG. 1, the extracellular portion of IL1-R1 fused with IgG-Fc domain (Fc-II) via a flexible linker may comprise the amino acid sequence of SEQ ID NO. 1, while IL-1RAcP fused with another IgG-Fc domain (Fc-V) via a flexible linker may comprise the amino acid sequence of SEQ. ID NO. 2.

In certain aspects, the present teachings provides for a recombinant DNA molecule having an open reading frame coding for a polypeptide comprising the leading 333 amino acids of the human IL1-R1 fused with IgG-Fc domain (Fc-II) via a flexible linker, and for another recombinant DNA molecule having an open reading frame coding for another polypeptide comprising the leading 358 amino acids of the human IL-1RAcP fused with another IgG-Fc domain (Fc-V) via a flexible linker.

In an example embodiment, the polypeptide comprising the leading 333 amino acids of the human IL1-R1 fused with IgG-Fc domain (Fc-II) via a flexible linker comprises the amino acid sequence of SEQ. ID NO. 3. The corresponding to it DNA molecule may comprise the nucleotide sequence of SEQ ID NO. 4. The another polypeptide comprises the leading 358 amino acids of the human IL-1RAcP fused with another IgG-Fc domain (Fc-V) via a flexible linker may comprise the amino acid sequence of SEQ. ID NO. 5. The corresponding to it DNA molecule may comprise the nucleotide sequence of SEQ ID NO. 6.

```
hIL1-R1-hIgG1-Fc polypeptide
                                                              (SEQ ID NO. 1)
LEADKCKERE EKIILVSSAN EIDVRPCPLN PNEHKGTITW YKDDSKTPVS TEQASRIHQH  60

KEKLWFVPAK VEDSGHYYCV VRNSSYCLRI KISAKFVENE PNLCYNAQAI FKQKLPVAGD 120

GGLVCPYMEF FKNENNELPK LQWYKDCKPL LLDNIHFSGV KDRLIVMNVA EKHRGNYTCH 180

ASYTYLGKQY PITRVIEFIT LEENKPTRPV IVSPANETME VDLGSQIQLI CNVTGQLSDI 240

AYWKWNGSVI DEDDPVLGED YYSVENPANK RRSTLITVLN ISEIESRFYK HPFTCFAKNT 300

HGIDAAYIQL IYPVTNGSGG GDKTHTCPPC PAPELLGGPS VFLFPPKPKD TLMISRTPEV 360

TCVVVDVSHE DPEVKFNWYV DGVEVHNAKT KPREEQYNST YRVVSVLTVL HQDWLNGKEY 420

KCKVSNKALP APIEKTISKA KGQPREPQVC TLPPSRDELT KNQVSLSCAV KGFYPSDIAV 480

EWESNGQPEN NYKTTPPVLD SDGSFKLVSK LTVDKSRWQQ GNVFSCSVMH EALHNHYTQK 540

SLSLSPGK                                                           548 hIL-1RAcP-hIgG1-Fc polypeptide
                                                              (SEQ ID NO. 2)
SERCDDWGLD TMRQIQVFED EPARIKCPLF EHFLKFNYST AHSAGLTLIW YWTRQDRDLE  60

EPINFRLPEN RISKEKDVLW FRPTLLNDTG NYTCMLRNTT YCSKVAFPLE VVQKDSCFNS 120

PMKLPVHKLY IEYGIQRITC PNVDGYFPSS VKPTITWYMG CYKIQNFNNV IPEGMNLSFL 180

IALISNNGNY TCVVTYPENG RTFHLTRTLT VKVVGSPKNA VPPVIHSPND HVVYEKEPGE 240

ELLIPCTVYF SFLMDSRNEV WWTIDGKKPD DITIDVTINE SISHSRTEDE TRTQILSIKK 300

VTSEDLKRSY VCHARSAKGE VAKAAKVKQK VPAPRYTVGS GGGDKTHTCP PCPAPELLGG 360

PSVFLFPPKP KDTLMISRTP EVTCVVVDVS HEDPEVKFNW YVDGVEVHNA KTKPREEQYN 420

STYRVVSVLT VLHQDWLNGK EYKCKVSNKA LPAPIEKTIS KAKGQPREPQ VYTLPPCRDE 480

LTKNQVSLWC LVKGFYPSDI AVEWESNGQP ENNYKTTPPV LDSDGSFFLY SALTVDKSRW 540

QQGNVFSCSV MHEALHNHYT QKSLSLSPGK                                   570
``` hIL1-R1-hIgG1-Fc polypeptide
(SEQ ID NO. 3)

| | | | | | |
|---|---|---|---|---|---|
| MKVLLRLICF | IALLISSLEA | DKCKEREEKI | ILVSSANEID | VRPCPLNPNE | HKGTITWYKD 60 |
| DSKTPVSTEQ | ASRIHQHKEK | LWFVPAKVED | SGHYYCVVRN | SSYCLRIKIS | AKFVENEPNL 120 |
| CYNAQAIFKQ | KLPVAGDGGL | VCPYMEFFKN | ENNELPKLQW | YKDCKPLLLD | NIHFSGVKDR 180 |
| LIVMNVAEKH | RGNYTCHASY | TYLGKQYPIT | RVIEFITLEE | NKPTRPVIVS | PANETMEVDL 240 |
| GSQIQLICNV | TGQLSDIAYW | KWNGSVIDED | DPVLGEDYYS | VENPANKRRS | TLITVLNISE 300 |
| IESRFYKHPF | TCFAKNTHGI | DAAYIQLIYP | VTNGSGGGDK | THTCPPCPAP | ELLGGPSVFL 360 |
| FPPKPKDTLM | ISRTPEVTCV | VVDVSHEDPE | VKFNWYVDGV | EVHNAKTKPR | EEQYNSTYRV 420 |
| VSVLTVLHQD | WLNGKEYKCK | VSNKALPAPI | EKTISKAKGQ | PREPQVCTLP | PSRDELTKNQ 480 |
| VSLSCAVKGF | YPSDIAVEWE | SNGQPENNYK | TTPPVLDSDG | SFKLVSKLTV | DKSRWQQGNV 540 |
| FSCSVMHEAL | HNHYTQKSLS | LSPGK | | | 565 | hIL1-R1-hIgG1-Fc DNA
(SEQ ID NO. 4)

| | | | | | |
|---|---|---|---|---|---|
| ATGAAGGTCC | TGCTCAGGCT | GATCTGCTTC | ATTGCCCTGC | TCATCAGCAG | CCTGGAAGCC 60 |
| GACAAGTGCA | AGGAGAGGGA | GGAGAAGATC | ATCCTCGTCA | GCTCCGCCAA | CGAGATTGAT 120 |
| GTCAGGCCCT | GCCCCCTCAA | CCCCAATGAG | CACAAGGGCA | CAATCACCTG | GTACAAGGAC 180 |
| GACAGCAAGA | CCCCTGTCTC | CACCGAGCAG | GCCAGCAGAA | TCCACCAGCA | CAAAGAGAAG 240 |
| CTGTGGTTCG | TGCCTGCCAA | GGTGGAAGAC | AGCGGCCACT | ACTACTGTGT | GGTGAGGAAC 300 |
| AGCTCCTACT | GCCTCAGGAT | CAAGATCTCC | GCCAAGTTCG | TGGAGAACGA | GCCCAACCTC 360 |
| TGTTACAACG | CTCAGGCTAT | TTTCAAGCAA | AAGCTCCCCG | TGGCTGGAGA | CGGAGGCCTG 420 |
| GTCTGTCCCT | ACATGGAGTT | CTTCAAGAAT | GAGAATAATG | AGCTCCCCAA | GCTCCAGTGG 480 |
| TACAAGGACT | GTAAGCCTCT | GCTCCTGGAC | AACATCCACT | TCTCCGGCGT | GAAGGACAGA 540 |
| CTGATCGTCA | TGAACGTGGC | CGAGAAGCAC | AGGGGAAACT | ACACCTGTCA | CGCCTCCTAC 600 |
| ACCTACCTCG | GCAAGCAATA | TCCCATCACC | AGGGTCATCG | AGTTCATCAC | CCTCGAAGAG 660 |
| AACAAGCCCA | CAAGGCCTGT | CATCGTCAGC | CCCGCCAATG | AAACCATGGA | GGTGGACCTC 720 |
| GGCAGCCAGA | TCCAGCTGAT | CTGCAACGTG | ACAGGCCAGC | TCAGCGACAT | TGCCTACTGG 780 |
| AAGTGGAACG | GCTCCGTGAT | CGACGAAGAT | GATCCCGTGC | TGGGCGAGGA | CTACTATAGC 840 |
| GTGGAGAACC | CCGCCAACAA | AAGAAGGAGC | ACCCTGATCA | CCGTGCTGAA | CATCAGCGAG 900 |
| ATCGAGTCCA | GATTCTATAA | GCATCCTTTC | ACCTGCTTTG | CCAAGAACAC | CCACGGCATC 960 |
| GACGCCGCTT | ACATCCAGCT | GATCTATCCC | GTGACCAACG | GATCCGGTGG | AGGTGACAAA 1020 |
| ACTCACACAT | GCCCACCGTG | CCCAGCTCCG | GAACTCCTGG | GCGGACCGTC | AGTCTTCCTC 1080 |
| TTCCCCCCAA | AACCCAAGGA | CACCCTCATG | ATCTCCCGGA | CCCCTGAGGT | CACATGCGTG 1140 |
| GTGGTGGACG | TGAGCCACGA | AGACCCTGAG | GTCAAGTTCA | ACTGGTACGT | GGACGGCGTG 1200 |
| GAGGTGCATA | ATGCCAAGAC | AAAGCCGCGG | GAGGAGCAGT | ACAACAGCAC | GTACCGTGTG 1260 |
| GTCAGCGTCC | TCACCGTCCT | GCACCAGGAC | TGGCTGAATG | GCAAGGAGTA | CAAGTGCAAG 1320 |
| GTCTCCAACA | AAGCCCTCCC | AGCCCCCATC | GAGAAAACCA | TCTCCAAAGC | CAAGGGCAG 1380 |
| CCCCGAGAAC | CACAGGTGTG | TACCCTGCCC | CCATCCCGGG | ATGAGCTGAC | CAAGAACCAG 1440 |
| GTCAGCCTGA | GTTGCGCGGT | CAAAGGCTTC | TATCCCAGCG | ACATCGCCGT | GGAGTGGGAG 1500 |
| AGCAATGGGC | AGCCGGAGAA | CAACTACAAG | ACCACGCCTC | CCGTGTTGGA | CTCCGACGGC 1560 |
| TCCTTCAAGC | TCGTCAGCAA | GCTCACCGTG | GACAAGAGCA | GGTGGCAGCA | GGGGAACGTC 1620 |
| TTCTCATGCT | CCGTGATGCA | TGAGGCTCTG | CACAACCACT | ACACGCAGAA | GAGCCTCTCC 1680 |
| CTGTCTCCGG | GTAAA | | | | 1695 |

-continued hIL-1RAcP-hIgG1-Fc polypeptide
(SEQ ID NO. 5)

```
MTLLWCVVSL YFYGILQSDA SERCDDWGLD TMRQIQVFED EPARIKCPLF EHFLKFNYST  60

AHSAGLTLIW YWTRQDRDLE EPINFRLPEN RISKEKDVLW FRPTLLNDTG NYTCMLRNTT 120

YCSKVAFPLE VVQKDSCFNS PMKLPVHKLY IEYGIQRITC PNVDGYFPSS VKPTITWYMG 180

CYKIQNFNNV IPEGMNLSFL IALISNNGNY TCVVTYPENG RTFHLTRTLT VKVVGSPKNA 240

VPPVIHSPND HVVYEKEPGE ELLIPCTVYF SFLMDSRNEV WWTIDGKKPD DITIDVTINE 300

SISHSRTEDE TRTQILSIKK VTSEDLKRSY VCHARSAKGE VAKAAKVKQK VPAPRYTVGS 360

GGGDKTHTCP PCPAPELLGG PSVFLFPPKP KDTLMISRTP EVTCVVVDVS HEDPEVKFNW 420

YVDGVEVHNA KTKPREEQYN STYRVVSVLT VLHQDWLNGK EYKCKVSNKA LPAPIEKTIS 480

KAKGQPREPQ VYTLPPCRDE LTKNQVSLWC LVKGFYPSDI AVEWESNGQP ENNYKTTPPV 540

LDSDGSFFLY SALTVDKSRW QQGNVFSCSV MHEALHNHYT QKSLSLSPGK           590
``` hIL-1RAcP-hIgG1-Fc DNA
(SEQ ID NO. 6)

```
ATGACTCTGC TGTGGTGCGT CGTGTCCCTC TACTTCTACG GCATCCTCCA GTCCGACGCC   60

AGCGAGAGGT GCGATGACTG GGGCCTGGAC ACCATGAGGC AGATCCAGGT GTTTGAGGAC  120

GAGCCTGCCA GGATTAAGTG CCCCCTCTTC GAGCACTTTC TGAAGTTCAA CTACAGCACC  180

GCTCACAGCG CTGGCCTGAC ACTGATCTGG TACTGGACAA GGCAGGACAG GGATCTCGAG  240

GAGCCCATCA ACTTCAGGCT GCCCGAAAAC AGAATCAGCA AGGAGAAGGA CGTGCTGTGG  300

TTCAGACCCA CCCTCCTCAA CGACACAGGC AACTACACCT GCATGCTCAG GAACACCACC  360

TACTGCAGCA AGGTGGCCTT CCCTCTCGAG GTGGTCCAGA AGGACAGCTG CTTCAACAGC  420

CCCATGAAGC TGCCCGTCCA TAAACTGTAC ATCGAGTACG GCATCCAGAG GATCACATGC  480

CCCAACGTGG ACGGCTACTT CCCCAGCTCC GTGAAGCCCA CCATCACATG GTACATGGGC  540

TGTTACAAAA TCCAGAACTT TAACAACGTC ATCCCCGAGG GCATGAATCT GTCCTTCCTG  600

ATCGCCCTGA TCAGCAACAA CGGCAATTAC ACCTGCGTCG TGACCTACCC CGAAAACGGC  660

AGGACCTTCC ACCTGACCAG GACCCTGACC GTGAAAGTCG TGGGAAGCCC CAAGAATGCC  720

GTGCCCCCCG TGATCCATTC CCCCAACGAC CACGTGGTGT ACGAGAAGGA GCCTGGAGAG  780

GAGCTGCTGA TCCCCTGCAC AGTGTACTTC TCCTTCCTGA TGGACTCCAG GAATGAAGTG  840

TGGTGGACCA TCGACGGCAA GAAGCCTGAC GACATCACCA TCGATGTGAC CATCAACGAG  900

AGCATCAGCC ACAGCAGGAC CGAGGACGAG ACCAGGACCC AGATCCTGAG CATCAAGAAA  960

GTCACCAGCG AGGACCTCAA GAGAAGCTAC GTCTGTCACG CCAGAAGCGC CAAAGGCGAG 1020

GTGGCCAAGG CTGCTAAGGT GAAACAGAAA GTGCCCGCTC CTAGGTACAC AGTCGGATCC 1080

GGTGGAGGTG ACAAAACTCA CACATGCCCA CCGTGCCCAG CTCCGGAACT CCTGGGCGGA 1140

CCGTCAGTCT TCCTCTTCCC CCCAAAACCC AAGGACACCC TCATGATCTC CCGGACCCCT 1200

GAGGTCACAT GCGTGGTGGT GGACGTGAGC CACGAAGACC CTGAGGTCAA GTTCAACTGG 1260

TACGTGGACG GCGTGGAGGT GCATAATGCC AAGACAAAGC CGCGGGAGGA GCAGTACAAC 1320

AGCACGTACC GTGTGGTCAG CGTCCTCACC GTCCTGCACC AGGACTGGCT GAATGGCAAG 1380

GAGTACAAGT GCAAGGTCTC CAACAAAGCC CTCCCAGCCC CCATCGAGAA AACCATCTCC 1440

AAAGCCAAAG GCAGCCCCG AGAACCACAG GTGTACACCC TGCCCCCATG TCGGGATGAG 1500

CTGACCAAGA ACCAGGTCAG CCTGTGGTGC CTGGTCAAAG GCTTCTATCC CAGCGACATC 1560

GCCGTGGAGT GGGAGAGCAA TGGGCAGCCG GAGAACAACT ACAAGACCAC GCCTCCCGTG 1620

TTGGACTCCG ACGGCTCCTT CTTCCTCTAC AGCGCGCTCA CCGTGGACAA GAGCAGGTGG 1680
```

-continued
```
CAGCAGGGGA ACGTCTTCTC ATGCTCCGTG ATGCATGAGG CTCTGCACAA CCACTACACG   1740

CAGAAGAGCC TCTCCCTGTC TCCGGGTAAA                                    1770
```

In certain aspects, the present invention provides for a recombinant mammalian expression plasmid for high expression of a polypeptide comprising the leading 333 amino acids of the human IL1-R1 fused with IgG-Fc domain (Fc-II) via a flexible linker, and for another recombinant DNA molecule having an open reading frame coding for another polypeptide comprising the leading 358 amino acids of the human IL-1RAcP fused with another IgG-Fc domain (Fc-V) via a flexible linker. This plasmid comprises two cytomegalovirus (CMV) promoters to drive transcription of the two genes coding for said polypeptide and said another polypeptide, each followed by a transcription termination sequence and a polyadenylation sequence. The plasmid also contains an origin of replication and a gene conferring ampicillin resistance, for supporting plasmid propagation and selection in bacteria. The plasmid further contains a gene for Glutamine synthetase, a selectable marker widely used for establishing stable CHOK1 and NSO cell lines.

In an example embodiment, the mammalian expression plasmid of the present teachings comprises the nucleotide sequence of SEQ ID NO. 7.

```
hIL1-R1-hIgG1-Fc-II/IL-1RAcP-hIgG1-Fc-V expression plasmid
                                                       (SEQ ID NO. 7)
AGCTTGCCAC CATGAAGGTC CTGCTCAGGC TGATCTGCTT CATTGCCCTG CTCATCAGCA     60

GCCTGGAAGC CGACAAGTGC AAGGAGAGGG AGGAGAAGAT CATCCTCGTC AGCTCCGCCA    120

ACGAGATTGA TGTCAGGCCC TGCCCCCTCA ACCCCAATGA GCACAAGGGC ACAATCACCT    180

GGTACAAGGA CGACAGCAAG ACCCCTGTCT CCACCGAGCA GGCCAGCAGA ATCCACCAGC    240

ACAAAGAGAA GCTGTGGTTC GTGCCTGCCA AGGTGGAAGA CAGCGGCCAC TACTACTGTG    300

TGGTGAGGAA CAGCTCCTAC TGCCTCAGGA TCAAGATCTC CGCCAAGTTC GTGGAGAACG    360

AGCCCAACCT CTGTTACAAC GCTCAGGCTA TTTTCAAGCA AAAGCTCCCC GTGGCTGGAG    420

ACGGAGGCCT GGTCTGTCCC TACATGGAGT TCTTCAAGAA TGAGAATAAT GAGCTCCCCA    480

AGCTCCAGTG GTACAAGGAC TGTAAGCCTC TGCTCCTGGA CAACATCCAC TTCTCCGGCG    540

TGAAGGACAG ACTGATCGTC ATGAACGTGG CCGAGAAGCA CAGGGGAAAC TACACCTGTC    600

ACGCCTCCTA CACCTACCTC GGCAAGCAAT ATCCCATCAC CAGGGTCATC GAGTTCATCA    660

CCCTCGAAGA GAACAAGCCC ACAAGGCCTG TCATCGTCAG CCCCGCCAAT GAAACCATGG    720

AGGTGGACCT CGGCAGCCAG ATCCAGCTGA TCTGCAACGT GACAGGCCAG CTCAGCGACA    780

TTGCCTACTG GAAGTGGAAC GGCTCCGTGA TCGACGAAGA TGATCCCGTG CTGGGCGAGG    840

ACTACTATAG CGTGGAGAAC CCCGCCAACA AAGAAGGAG CACCCTGATC ACCGTGCTGA    900

ACATCAGCGA GATCGAGTCC AGATTCTATA AGCATCCTTT CACCTGCTTT GCCAAGAACA    960

CCCACGGCAT CGACGCCGCT TACATCCAGC TGATCTATCC CGTGACCAAC GGATCCGGTG   1020

GAGGTGACAA AACTCACACA TGCCCACCGT GCCCAGCTCC GGAACTCCTG GGCGGACCGT   1080

CAGTCTTCCT CTTCCCCCCA AAACCCAAGG ACACCCTCAT GATCTCCCGG ACCCCTGAGG   1140

TCACATGCGT GGTGGTGGAC GTGAGCCACG AAGACCCTGA GGTCAAGTTC AACTGGTACG   1200

TGGACGGCGT GGAGGTGCAT AATGCCAAGA CAAAGCCGCG GGAGGAGCAG TACAACAGCA   1260

CGTACCGTGT GGTCAGCGTC CTCACCGTCC TGCACCAGGA CTGGCTGAAT GGCAAGGAGT   1320

ACAAGTGCAA GGTCTCCAAC AAAGCCCTCC CAGCCCCCAT CGAGAAAACC ATCTCCAAAG   1380

CCAAAGGGCA GCCCCGAGAA CCACAGGTGT GTACCCTGCC CCCATCCCGG GATGAGCTGA   1440

CCAAGAACCA GGTCAGCCTG AGTTGCGCGG TCAAAGGCTT CTATCCCAGC GACATCGCCG   1500

TGGAGTGGGA GAGCAATGGG CAGCCGGAGA ACAACTACAA GACCACGCCT CCCGTGTTGG   1560

ACTCCGACGG CTCCTTCAAG CTCGTCAGCA AGCTCACCGT GGACAAGAGC AGGTGGCAGC   1620

AGGGGAACGT CTTCTCATGC TCCGTGATGC ATGAGGCTCT GCACAACCAC TACACGCAGA   1680

AGAGCCTCTC CCTGTCTCCG GGTAAATAAT AGAATTCATT GATCATAATC AGCCATACCA   1740
```

```
                                          -continued
CATTTGTAGA GGTTTTACTT GCTTTAAAAA ACCTCCCACA CCTCCCCCTG AACCTGAAAC   1800

ATAAAATGAA TGCAATTGTT GTTGTTAACT TGTTTATTGC AGCTTATAAT GGTTACAAAT   1860

AAAGCAATAG CATCACAAAT TTCACAAATA AAGCATTTTT TTCACTGCAT TCTAGTTGTG   1920

GTTTGTCCAA ACTCATCAAT GTATCTTATC ATGTCTGGCG GCCGCCGATA TTTGAAAATA   1980

TGGCATATTG AAAATGTCGC CGATGTGAGT TTCTGTGTAA CTGATATCGC CATTTTTCCA   2040

AAAGTGATTT TTGGGCATAC GCGATATCTG GCGATAGCGC TTATATCGTT TACGGGGAT    2100

GGCGATAGAC GACTTTGGTG ACTTGGGCGA TTCTGTGTGT CGCAAATATC GCAGTTTCGA   2160

TATAGGTGAC AGACGATATG AGGCTATATC GCCGATAGAG GCGACATCAA GCTGGCACAT   2220

GGCCAATGCA TATCGATCTA TACATTGAAT CAATATTGGC CATTAGCCAT ATTATTCATT   2280

GGTTATATAG CATAAATCAA TATTGGCTAT TGGCCATTGC ATACGTTGTA TCCATATCAT   2340

AATATGTACA TTTATATTGG CTCATGTCCA ACATTACCGC CATGTTGACA TTGATTATTG   2400

ACTAGTTATT AATAGTAATC AATTACGGGG TCATTAGTTC ATAGCCCATA TATGGAGTTC   2460

CGCGTTACAT AACTTACGGT AAATGGCCCG CCTGGCTGAC CGCCCAACGA CCCCCGCCCA   2520

TTGACGTCAA TAATGACGTA TGTTCCCATA GTAACGCCAA TAGGGACTTT CCATTGACGT   2580

CAATGGGTGG AGTATTTACG GTAAACTGCC CACTTGGCAG TACATCAAGT GTATCATATG   2640

CCAAGTACGC CCCCTATTGA CGTCAATGAC GGTAAATGGC CCGCCTGGCA TTATGCCCAG   2700

TACATGACCT TATGGGACTT TCCTACTTGG CAGTACATCT ACGTATTAGT CATCGCTATT   2760

ACCATGGTGA TGCGGTTTTG GCAGTACATC AATGGGCGTG GATAGCGGTT TGACTCACGG   2820

GGATTTCCAA GTCTCCACCC CATTGACGTC AATGGGAGTT TGTTTTGGCA CCAAAATCAA   2880

CGGGACTTTC CAAAATGTCG TAACAACTCC GCCCCATTGA CGCAAATGGG CGGTAGGCGT   2940

GTACGGTGGG AGGTCTATAT AAGCAGAGCT CGTTTAGTGA ACCGTCAGAT CGCCTGGAGA   3000

CGCCATCCAC GCTGTTTTGA CCTCCATAGA AGACACCGGG ACCGATCCAG CCTCCGCGGC   3060

CGGGAACGGT GCATTGGAAC GCGGATTCCC CGTGCCAAGA GTGACGTAAG TACCGCCTAT   3120

AGAGTCTATA GGCCCACCCC CTTGGCTTCT TATGCATGCT ATACTGTTTT TGGCTTGGGG   3180

TCTATACACC CCCGCTTCCT CATGTTATAG GTGATGGTAT AGCTTAGCCT ATAGGTGTGG   3240

GTTATTGACC ATTATTGACC ACTCCCCTAT TGGTGACGAT ACTTTCCATT ACTAATCCAT   3300

AACATGGCTC TTTGCCACAA CTCTCTTTAT TGGCTATATG CCAATACACT GTCCTTCAGA   3360

GACTGACACG GACTCTGTAT TTTTACAGGA TGGGGTCTCA TTTATTATTT ACAAATTCAC   3420

ATATACAACA CCACCGTCCC CAGTGCCCGC AGTTTTTATT AAACATAACG TGGGATCTCC   3480

ACGCGAATCT CGGGTACGTG TTCCGGACAT GGGCTCTTCT CCGGTAGCGG CGGAGCTTCT   3540

ACATCCGAGC CCTGCTCCCA TGCCTCCAGC GACTCATGGT CGCTCGGCAG CTCCTTGCTC   3600

CTAACAGTGG AGGCCAGACT TAGGCACAGC ACGATGCCCA CCACCACCAG TGTGCCGCAC   3660

AAGGCCGTGG CGGTAGGGTA TGTGTCTGAA AATGAGCTCG GGGAGCGGGC TTGCACCGCT   3720

GACGCATTTG GAAGACTTAA GGCAGCGGCA GAAGAAGATG CAGGCAGCTG AGTTGTTGTG   3780

TTCTGATAAG AGTCAGAGGT AACTCCCGTT GCGGTGCTGT TAACGGTGGA GGGCAGTGTA   3840

GTCTGAGCAG TACTCGTTGC TGCCGCGCGC GCCACCAGAC ATAATAGCTG ACAGACTAAC   3900

AGACTGTTCC TTTCCATGGG TCTTTTCTGC AGTCACCGTC CTTGACACGA AGCTTGCCAC   3960

CATGACTCTG CTGTGGTGCG TCGTGTCCCT CTACTTCTAC GGCATCCTCC AGTCCGACGC   4020

CAGCGAGAGG TGCGATGACT GGGGCCTGGA CACCATGAGG CAGATCCAGG TGTTTGAGGA   4080

CGAGCCTGCC AGGATTAAGT GCCCCCTCTT CGAGCACTTT CTGAAGTTCA ACTACAGCAC   4140

CGCTCACAGC GCTGGCCTGA CACTGATCTG GTACTGGACA AGGCAGGACA GGGATCTCGA   4200
```

```
GGAGCCCATC AACTTCAGGC TGCCCGAAAA CAGAATCAGC AAGGAGAAGG ACGTGCTGTG    4260

GTTCAGACCC ACCCTCCTCA ACGACACAGG CAACTACACC TGCATGCTCA GGAACACCAC    4320

CTACTGCAGC AAGGTGGCCT TCCCTCTCGA GGTGGTCCAG AAGGACAGCT GCTTCAACAG    4380

CCCCATGAAG CTGCCCGTCC ATAAACTGTA CATCGAGTAC GGCATCCAGA GGATCACATG    4440

CCCCAACGTG GACGGCTACT TCCCCAGCTC CGTGAAGCCC ACCATCACAT GGTACATGGG    4500

CTGTTACAAA ATCCAGAACT TTAACAACGT CATCCCCGAG GGCATGAATC TGTCCTTCCT    4560

GATCGCCCTG ATCAGCAACA ACGGCAATTA CACCTGCGTC GTGACCTACC CCGAAAACGG    4620

CAGGACCTTC CACCTGACCA GGACCCTGAC CGTGAAAGTC GTGGGAAGCC CCAAGAATGC    4680

CGTGCCCCCC GTGATCCATT CCCCCAACGA CCACGTGGTG TACGAGAAGG AGCCTGGAGA    4740

GGAGCTGCTG ATCCCCTGCA CAGTGTACTT CTCCTTCCTG ATGGACTCCA GGAATGAAGT    4800

GTGGTGGACC ATCGACGGCA AGAAGCCTGA CGACATCACC ATCGATGTGA CCATCAACGA    4860

GAGCATCAGC CACAGCAGGA CCGAGGACGA GACCAGGACC CAGATCCTGA GCATCAAGAA    4920

AGTCACCAGC GAGGACCTCA AGAGAAGCTA CGTCTGTCAC GCCAGAAGCG CCAAAGGCGA    4980

GGTGGCCAAG GCTGCTAAGG TGAAACAGAA AGTGCCCGCT CCTAGGTACA CAGTCGGATC    5040

CGGTGGAGGT GACAAAACTC ACACATGCCC ACCGTGCCCA GCTCCGGAAC TCCTGGGCGG    5100

ACCGTCAGTC TTCCTCTTCC CCCCAAAACC CAAGGACACC CTCATGATCT CCCGGACCCC    5160

TGAGGTCACA TGCGTGGTGG TGGACGTGAG CCACGAAGAC CCTGAGGTCA AGTTCAACTG    5220

GTACGTGGAC GGCGTGGAGG TGCATAATGC CAAGACAAAG CCGCGGGAGG AGCAGTACAA    5280

CAGCACGTAC CGTGTGGTCA GCGTCCTCAC CGTCCTGCAC CAGGACTGGC TGAATGGCAA    5340

GGAGTACAAG TGCAAGGTCT CCAACAAAGC CCTCCCAGCC CCCATCGAGA AAACCATCTC    5400

CAAAGCCAAA GGGCAGCCCC GAGAACCACA GGTGTACACC CTGCCCCCAT GTCGGGATGA    5460

GCTGACCAAG AACCAGGTCA GCCTGTGGTG CCTGGTCAAA GGCTTCTATC CAGCGACAT    5520

CGCCGTGGAG TGGGAGAGCA ATGGGCAGCC GGAGAACAAC TACAAGACCA CGCCTCCCGT    5580

GTTGGACTCC GACGGCTCCT TCTTCCTCTA CAGCGCGCTC ACCGTGGACA AGAGCAGGTG    5640

GCAGCAGGGG AACGTCTTCT CATGCTCCGT GATGCATGAG GCTCTGCACA ACCACTACAC    5700

GCAGAAGAGC CTCTCCCTGT CTCCGGGTAA ATAATAGAAT TCATTGATCA TAATCAGCCA    5760

TACCACATTT GTAGAGGTTT TACTTGCTTT AAAAAACCTC CCACACCTCC CCCTGAACCT    5820

GAAACATAAA ATGAATGCAA TTGTTGTTGT TAACTTGTTT ATTGCAGCTT ATAATGGTTA    5880

CAAATAAAGC AATAGCATCA CAAATTTCAC AAATAAAGCA TTTTTTTCAC TGCATTCTAG    5940

TTGTGGTTTG TCCAAACTCA TCAATGTATC TTATCATGTC TGGATCCTCT ACGCCGGACG    6000

CATCGTGGCC GGCATCACCG CGCCACAGG TGCGGTTGCT GGCGCCTATA TCGCCGACAT    6060

CACCGATGGG GAAGATCGGG CTCGCCACTT CGGGCTCATG AGCGCTTGTT TCGGCGTGGG    6120

TATGGTGGCA GGCCCCGTGG CCGGGGGACT GTTGGGCGCC ATCTCCTTGC ATGCACCATT    6180

CCTTGCGGCG GCGGTGCTCA ACGGCCTCAA CCTACTACTG GGCTGCTTCC TAATGCAGGA    6240

GTCGCATAAG GGAGAGCGTC GACCTCGGGC CGCGTTGCTG GCGTTTTTCC ATAGGCTCCG    6300

CCCCCCTGAC GAGCATCACA AAAATCGACG CTCAAGTCAG AGGTGGCGAA ACCCGACAGG    6360

ACTATAAAGA TACCAGGCGT TTCCCCCTGG AAGCTCCCTC GTGCGCTCTC CTGTTCCGAC    6420

CCTGCCGCTT ACCGGATACC TGTCCGCCTT TCTCCCTTCG GGAAGCGTGG CGCTTTCTCA    6480

TAGCTCACGC TGTAGGTATC TCAGTTCGGT GTAGGTCGTT CGCTCCAAGC TGGGCTGTGT    6540

GCACGAACCC CCCGTTCAGC CCGACCGCTG CGCCTTATCC GGTAACTATC GTCTTGAGTC    6600
```

-continued

```
CAACCCGGTA AGACACGACT TATCGCCACT GGCAGCAGCC ACTGGTAACA GGATTAGCAG    6660

AGCGAGGTAT GTAGGCGGTG CTACAGAGTT CTTGAAGTGG TGGCCTAACT ACGGCTACAC    6720

TAGAAGAACA GTATTTGGTA TCTGCGCTCT GCTGAAGCCA GTTACCTTCG GAAAAAGAGT    6780

TGGTAGCTCT TGATCCGGCA AACAAACCAC CGCTGGTAGC GGTGGTTTTT TTGTTTGCAA    6840

GCAGCAGATT ACGCGCAGAA AAAAGGATC TCAAGAAGAT CCTTTGATCT TTTCTACGGG     6900

GTCTGACGCT CAGTGGAACG AAAACTCACG TTAAGGGATT TTGGTCATGA GATTATCAAA    6960

AAGGATCTTC ACCTAGATCC TTTTAAATTA AAAATGAAGT TTTAAATCAA TCTAAAGTAT    7020

ATATGAGTAA ACTTGGTCTG ACAGTTACCA ATGCTTAATC AGTGAGGCAC CTATCTCAGC    7080

GATCTGTCTA TTTCGTTCAT CCATAGTTGC CTGACTCCCC GTCGTGTAGA TAACTACGAT    7140

ACGGGAGGGC TTACCATCTG GCCCCAGTGC TGCAATGATA CCGCGAGACC CACGCTCACC    7200

GGCTCCAGAT TTATCAGCAA TAAACCAGCC AGCCGGAAGG GCCGAGCGCA GAAGTGGTCC    7260

TGCAACTTTA TCCGCCTCCA TCCAGTCTAT TAATTGTTGC CGGGAAGCTA GAGTAAGTAG    7320

TTCGCCAGTT AATAGTTTGC GCAACGTTGT TGCCATTGCT ACAGGCATCG TGGTGTCACG    7380

CTCGTCGTTT GGTATGGCTT CATTCAGCTC CGGTTCCCAA CGATCAAGGC GAGTTACATG    7440

ATCCCCCATG TTGTGCAAAA AAGCGGTTAG CTCCTTCGGT CCTCCGATCG TTGTCAGAAG    7500

TAAGTTGGCC GCAGTGTTAT CACTCATGGT TATGGCAGCA CTGCATAATT CTCTTACTGT    7560

CATGCCATCC GTAAGATGCT TTTCTGTGAC TGGTGAGTAC TCAACCAAGT CATTCTGAGA    7620

ATAGTGTATG CGGCGACCGA GTTGCTCTTG CCCGGCGTCA ATACGGGATA ATACCGCGCC    7680

ACATAGCAGA ACTTTAAAAG TGCTCATCAT TGGAAAACGT TCTTCGGGGC GAAAACTCTC    7740

AAGGATCTTA CCGCTGTTGA GATCCAGTTC GATGTAACCC ACTCGTGCAC CCAACTGATC    7800

TTCAGCATCT TTTACTTTCA CCAGCGTTTC TGGGTGAGCA AAAACAGGAA GGCAAAATGC    7860

CGCAAAAAAG GGAATAAGGG CGACACGGAA ATGTTGAATA CTCATACTCT TCCTTTTTCA    7920

ATATTATTGA AGCATTATC AGGGTTATTG TCTCATGAGC GGATACATAT TTGAATGTAT     7980

TTAGAAAAAT AAACAAATAG GGGTTCCGCG CACATTTCCC CGAAAAGTGC CACCTGACGT    8040

CTAAGAAACC ATTATTATCA TGACATTAAC CTATAAAAAT AGGCGTATCA CGAGGCCCTG    8100

ATGGCTCTTT GCGGCACCCA TCGTTCGTAA TGTTCCGTGG CACCGAGGAC AACCCTCAAG    8160

AGAAAATGTA ATCACACTGG CTCACCTTCG GGTGGGCCTT TCTGCGTTTA TAAGGAGACA    8220

CTTTATGTTT AAGAAGGTTG GTAAATTCCT TGCGGCTTTG GCAGCCAAGC TAGATCCGGC    8280

TGTGGAATGT GTGTCAGTTA GGGTGTGGAA AGTCCCCAGG CTCCCCAGCA GGCAGAAGTA    8340

TGCAAAGCAT GCATCTCAAT TAGTCAGCAA CCAGGTGTGG AAAGTCCCCA GGCTCCCCAG    8400

CAGGCAGAAG TATGCAAAGC ATGCATCTCA ATTAGTCAGC AACCATAGTC CGCCCCTAA    8460

CTCCGCCCAT CCCGCCCCTA ACTCCGCCCA GTTCCGCCCA TTCTCCGCCC CATGGCTGAC    8520

TAATTTTTTT TATTTATGCA GAGGCCGAGG CCGCCTCGGC CTCTGAGCTA TTCCAGAAGT    8580

AGTGAGGAGG CTTTTTTGGA GGCCTAGGCT TTTGCAAAAA GCTAGCTTGG GGCCACCGCT    8640

CAGAGCACCT TCCACCATGG CCACCTCAGC AAGTTCCCAC TTGAACAAAA ACATCAAGCA    8700

AATGTACTTG TGCCTGCCCC AGGGTGAGAA AGTCCAAGCC ATGTATATCT GGGTTGATGG    8760

TACTGGAGAA GGACTGCGCT GCAAAACCCG CACCCTGGAC TGTGAGCCCA AGTGTGTAGA    8820

AGAGTTACCT GAGTGGAATT TGATGGCTC TAGTACCTTT CAGTCTGAGG GCTCCAACAG     8880

TGACATGTAT CTCAGCCCTG TTGCCATGTT TCGGGACCCC TTCCGCAGAG ATCCCAACAA    8940

GCTGGTGTTC TGTGAAGTTT TCAAGTACAA CCGGAAGCCT GCAGAGACCA ATTTAAGGCA    9000

CTCGTGTAAA CGGATAATGG ACATGGTGAG CAACCAGCAC CCCTGGTTTG GAATGGAACA    9060
```

-continued

```
GGAGTATACT CTGATGGGAA CAGATGGGCA CCCTTTTGGT TGGCCTTCCA ATGGCTTTCC    9120

TGGGCCCCAA GGTCCGTATT ACTGTGGTGT GGGCGCAGAC AAAGCCTATG CAGGGATAT     9180

CGTGGAGGCT CACTACCGCG CCTGCTTGTA TGCTGGGGTC AAGATTACAG GAACAAATGC    9240

TGAGGTCATG CCTGCCCAGT GGGAACTCCA AATAGGACCC TGTGAAGGAA TCCGCATGGG    9300

AGATCATCTC TGGGTGGCCC GTTTCATCTT GCATCGAGTA TGTGAAGACT TTGGGGTAAT    9360

AGCAACCTTT GACCCCAAGC CCATTCCTGG GAACTGGAAT GGTGCAGGCT GCCATACCAA    9420

CTTTAGCACC AAGGCCATGC GGGAGGAGAA TGGTCTGAAG CACATCGAGG AGGCCATCGA    9480

GAAACTAAGC AAGCGGCACC GGTACCACAT TCGAGCCTAC GATCCCAAGG GGGGCCTGGA    9540

CAATGCCCGT GGTCTGACTG GGTTCCACGA AACGTCCAAC ATCAACGACT TTTCTGCTGG    9600

TGTCGCCAAT CGCAGTGCCA GCATCCGCAT TCCCCGGACT GTCGGCCAGG AGAAGAAAGG    9660

TTACTTTGAA GACCGCGGCC CCTCTGCCAA TTGTGACCCC TTTGCAGTGA CAGAAGCCAT    9720

CGTCCGCACA TGCCTTCTCA ATGAGACTGG CGACGAGCCC TTCCAATACA AAACTAATT     9780

AGACTTTGAG TGATCTTGAG CCTTTCCTAG TTCATCCCAC CCCGCCCCAG AGAGATCTTT    9840

GTGAAGGAAC CTTACTTCTG TGGTGTGACA TAATTGGACA AACTACCTAC AGAGATTTAA    9900

AGCTCTAAGG TAAATATAAA ATTTTTAAGT GTATAATGTG TTAAACTACT GATTCTAATT    9960

GTTTGTGTAT TTTAGATTCC AACCTATGGA ACTGATGAAT GGGAGCAGTG GTGGAATGCC   10020

TTTAATGAGG AAAACCTGTT TTGCTCAGAA GAAATGCCAT CTAGTGATGA TGAGGCTACT   10080

GCTGACTCTC AACATTCTAC TCCTCCAAAA AAGAAGAGAA AGGTAGAAGA CCCCAAGGAC   10140

TTTCCTTCAG AATTGCTAAG TTTTTTGAGT CATGCTGTGT TTAGTAATAG AACTCTTGCT   10200

TGCTTTGCTA TTTACACCAC AAAGGAAAAA GCTGCACTGC TATACAAGAA AATTATGGAA   10260

AAATATTCTG TAACCTTTAT AAGTAGGCAT AACAGTTATA ATCATAACAT ACTGTTTTTT   10320

CTTACTCCAC ACAGGCATAG AGTGTCTGCT ATTAATAACT ATGCTCAAAA ATTGTGTACC   10380

TTTAGCTTTT TAATTTGTAA AGGGGTTAAT AAGGAATATT TGATGTATAG TGCCTTGACT   10440

AGAGATCATA ATCAGCCATA CCACATTTGT AGAGGTTTTA CTTGCTTTAA AAAACCTCCC   10500

ACACCTCCCC CTGAACCTGA AACATAAAAT GAATGCAATT GTTGTTGTTA ACTTGTTTAT   10560

TGCAGCTTAT AATGGTTACA AATAAAGCAA TAGCATCACA AATTTCACAA ATAAAGCATT   10620

TTTTTCACTG CATTCTAGTT GTGGTTTGTC CAAACTCATC AATGTATCTT ATCATGTCTG   10680

GATCTAGCTT CGTGTCAAGG ACGGTGACTG CAGTGAATAA TAAAATGTGT GTTTGTCCGA   10740

AATACGCGTT TTGAGATTTC TGTCGCCGAC TAAATTCATG TCGCGCGATA GTGGTGTTTA   10800

TCGCCGATAG AGATGGCGAT ATTGGAAAAA TCGATATTTG AAAATATGGC ATATTGAAAA   10860

TGTCGCCGAT GTGAGTTTCT GTGTAACTGA TATCGCCATT TTTCCAAAAG TGATTTTTGG   10920

GCATACGCGA TATCTGGCGA TAGCGCTTAT ATCGTTTACG GGGATGGCG ATAGACGACT     10980

TTGGTGACTT GGGCGATTCT GTGTGTCGCA AATATCGCAG TTTCGATATA GGTGACAGAC   11040

GATATGAGGC TATATCGCCG ATAGAGGCGA CATCAAGCTG GCACATGGCC AATGCATATC   11100

GATCTATACA TTGAATCAAT ATTGGCCATT AGCCATATTA TTCATTGGTT ATATAGCATA   11160

AATCAATATT GGCTATTGGC CATTGCATAC GTTGTATCCA TATCATAATA TGTACATTTA   11220

TATTGGCTCA TGTCCAACAT TACCGCCATG TTGACATTGA TTATTGACTA GTTATTAATA   11280

GTAATCAATT ACGGGGTCAT TAGTTCATAG CCCATATATG GAGTTCCGCG TTACATAACT   11340

TACGGTAAAT GGCCCGCCTG GCTGACCGCC AACGACCCC CGCCCATTGA CGTCAATAAT     11400

GACGTATGTT CCCATAGTAA CGCCAATAGG GACTTTCCAT TGACGTCAAT GGGTGGAGTA   11460
```

```
                                    -continued
TTTACGGTAA ACTGCCCACT TGGCAGTACA TCAAGTGTAT CATATGCCAA GTACGCCCCC  11520

TATTGACGTC AATGACGGTA AATGGCCCGC CTGGCATTAT GCCCAGTACA TGACCTTATG  11580

GGACTTTCCT ACTTGGCAGT ACATCTACGT ATTAGTCATC GCTATTACCA TGGTGATGCG  11640

GTTTTGGCAG TACATCAATG GGCGTGGATA GCGGTTTGAC TCACGGGGAT TTCCAAGTCT  11700

CCACCCCATT GACGTCAATG GGAGTTTGTT TTGGCACCAA AATCAACGGG ACTTTCCAAA  11760

ATGTCGTAAC AACTCCGCCC CATTGACGCA AATGGGCGGT AGGCGTGTAC GGTGGGAGGT  11820

CTATATAAGC AGAGCTCGTT TAGTGAACCG TCAGATCGCC TGGAGACGCC ATCCACGCTG  11880

TTTTGACCTC CATAGAAGAC ACCGGGACCG ATCCAGCCTC CGCGGCCGGG AACGGTGCAT  11940

TGGAACGCGG ATTCCCCGTG CCAAGAGTGA CGTAAGTACC GCCTATAGAG TCTATAGGCC  12000

CACCCCCTTG GCTTCTTATG CATGCTATAC TGTTTTTGGC TTGGGGTCTA TACACCCCCG  12060

CTTCCTCATG TTATAGGTGA TGGTATAGCT TAGCCTATAG GTGTGGGTTA TTGACCATTA  12120

TTGACCACTC CCCTATTGGT GACGATACTT TCCATTACTA ATCCATAACA TGGCTCTTTG  12180

CCACAACTCT CTTTATTGGC TATATGCCAA TACACTGTCC TTCAGAGACT GACACGGACT  12240

CTGTATTTTT ACAGGATGGG GTCTCATTTA TTATTTACAA ATTCACATAT ACAACACCAC  12300

CGTCCCCAGT GCCCGCAGTT TTTATTAAAC ATAACGTGGG ATCTCCACGC GAATCTCGGG  12360

TACGTGTTCC GGACATGGGC TCTTCTCCGG TAGCGGCGGA GCTTCTACAT CCGAGCCCTG  12420

CTCCCATGCC TCCAGCGACT CATGGTCGCT CGGCAGCTCC TTGCTCCTAA CAGTGGAGGC  12480

CAGACTTAGG CACAGCACGA TGCCCACCAC CACCAGTGTG CCGCACAAGG CCGTGGCGGT  12540

AGGGTATGTG TCTGAAAATG AGCTCGGGGA GCGGGCTTGC ACCGCTGACG CATTTGGAAG  12600

ACTTAAGGCA GCGGCAGAAG AAGATGCAGG CAGCTGAGTT GTTGTGTTCT GATAAGAGTC  12660

AGAGGTAACT CCCGTTGCGG TGCTGTTAAC GGTGGAGGGC AGTGTAGTCT GAGCAGTACT  12720

CGTTGCTGCC GCGCGCGCCA CCAGACATAA TAGCTGACAG ACTAACAGAC TGTTCCTTTC  12780

CATGGGTCTT TTCTGCAGTC ACCGTCCTTG ACACGA                             12816
```

In certain aspects, the present teachings provide for a mammalian expression system for production of a heterodimeric protein assembly comprising a polypeptide comprising amino acid residues 18 through 333 of the human IL1-R1 fused with IgG-Fc domain (Fc-II) via a flexible linker, and another polypeptide comprising amino acid residues 21 through 358 of the human IL-1RAcP fused with another IgG-Fc domain (Fc-V) via a flexible linker.

In an example embodiment, the mammalian expression system of the present invention comprises Chinese hamster ovary cells (CHO-K1) harboring a plasmid comprising nucleotide sequence of SEQ ID NO. 7.

In certain aspects, the present teachings provide for a method of treatment of a mammal effected by the following disorders associated with IL-1β modulation: arthritis, a gout, a rheumatoid arthritis, a Cryopyrin-Associated Periodic Syndromes (CAPS), a scleroderma, a diabetes, a atherosclerosis, a dry eye disease, an ocular allergy, or an uveitis.

EXAMPLES

The following Examples illustrate the forgoing aspects and other aspects of the present teachings. These non-limiting Examples are put forth so as to provide those of ordinary skill in the art with illustrative embodiments as to how the compounds, compositions, articles, devices, and/or methods claimed herein are made and evaluated. The Examples are intended to be purely exemplary of the inventions disclosed herein and are not intended to limit the scope of what the inventors regard as their invention. Efforts have been made to ensure accuracy with respect to numbers (e.g., amounts, temperature, etc.) but some errors and deviations should be accounted for.

Example 1: Preparation of Polypeptides of the Present Invention hIL1-R1-hIgG1-Fc polypeptide of SEQ ID NO. 1 and hIL-1RAcP-hIgG1-Fc polypeptide of SEQ ID NO. 2 were co-expressed in CHO-K1 using molecular biology, cell culture and protein biochemistry techniques known in the art and described in PCT Publication WO/2014/035361, and PCT Application Serial No. PCT/US/2013/026349. Essentially, CHO-K1 cells expressing the polypeptides were harvested and lysed utilizing well established protocols. After cell lysate clarification, the supernatant containing expressed polypeptides was first applied to a Protein A affinity column. The pH adjusted Protein A column eluate was further purified by anion-exchange chromatography (AIEX) utilizing Q Sepharose resin. The AIEX flowthrough was analyzed by size-exclusion HPLC (SEC-HPLC), SDS-PAGE and other analytical techniques, as appropriate.

For subsequent studies, a therapeutic composition comprising hIL1-R1-hIgG1-Fc and hIL-1RAcP-hIgG1-Fc polypeptides was formulated to contain 20 mg/ml of the polypeptides, 6% (m/v) sucrose, 3% (m/v) PEG3350, 50 mM sodium chloride, and 20 mM L-Histidine pH 6.5.

Example 2: Evaluation of Polypeptides of the Present Teachings Affinity Binding to RANKL Using Surface Plasmon Resonance (SPR) Assay The binding affinity of prepared polypeptides of IL1R-FcV-RAcP-FcII heterodimer (SEQ ID NO.1 and SEQ ID NO. 2) to IL-1β/IL-1F2 (NCBI Accession # NP_000567) was measured using a specially designed Surface Plasmon Resonance (SPR) assay. The assay was carried out using capturing method where anti-human IgG were cross-linked to the surface of sensor chip for capturing IL1R-FcV-RAcP-FcII heterodimer via its IgG (Fc) fragments. Series of different concentrations of IL-1β/IL-1F2 were used for calculation of the dissociation constant (Kd).

Reagents and Equipment:
Equipment:
BiaCore T200, Instrument #12108, GE Healthcare, with Biacore T200 Control and Evaluation Software packages.
Reagents:
IL1R-FcV-RAcP-FcII heterodimer stock solution 20 mg/ml of the polypeptides, 6% (m/v) sucrose, 3% (m/v) PEG3350, 50 mM sodium chloride, and 20 mM L-Histidine pH 6.5.
IL-1β/IL-1F2, Human recombinant, *E. coli*-derived, Ala117-Ser269, Accession #NP_000567, R&D systems, Cat #201-LB, Lot # AD1412111
Sensor Chip CM5, Series S, GE Healthcare BR-1005-30, Lot #10189577
Human Antibody Capture Kit, GE Healthcare, Cat # BR-1008-39, Lot #10202616;
HBS-EP+10× running buffer, GE Healthcare, Cat # BR-1006-69;

Procedures:
Anti-Human IgG Conjugation:
Conjugation procedure for anti-human IgG (Fc) was carried out according manufacturer's protocol using conditions below.
1. CM5 Sensor Chip was placed into the instrument and primed with Biacore running buffer, 1×HBS-EP, for 6 min at 10 μl/min, repeated twice. All steps were carried out at 25° C. Channels 1 and 2 was used for the experiment and channels 3 and 4 were reserved as a backup;
2. Anti-Human IgG from the kit, 0.5 mg/ml in 0.15 M NaCl, was diluted 20-fold in Immobilization Buffer (10 mM Na-acetate pH 5.0) to a final concentration of 25 μg/ml;
3. Reagents for immobilization procedure were prepared as follows: EDC (1-ethyl-3-(3-dimethylaminopropyl)-carbodiimide)—0.4 M in Milli-Q water; NHS (N-hydroxysuccinimide)—0.1 M in Milli-Q water; 1 M Ethanolamine-HCl pH 8.5 in Milli-Q water;
4. Standard protocol for surface activation and immobilization was used;
5. Activation: EDC and NHS were mixed at 1:1 ratio and injected into the chip at 10 μl/min for 7 min;
6. Immobilization: Anti-Human IgG were injected into the chip at 10 μl/min for 5 min;
7. Deactivation: Unreacted active groups were blocked by injection of 1 M Ethanolamine-HCL at 10 μl/min for 7 min;
8. After antibody conjugation, the chip was washed with 1×HBS-EP 2 times at 10 μl/min for 6 min and then the "dry" working cycle without addition of any protein component was run twice. The working cycle consisted of Ligand (IL1R-FcV-RAcP-FcII heterodimer) Loading Step of 1 min, Wash Step of 3 min, Sample (IL-1) Loading Step of 1 min, Wash step of 16.7 min, Chip Regeneration Step, 1 min, 3 M $MgCl_2$. All steps were run at 10 μl/min except Sample Loading Step that was run at 30 μl/min;

Experimental Data:
Affinity evaluation of IL1R-FcV-RAcP-FcII heterodimer/IL-1β/IL-1F2 interaction.

The goal of this experiment was to measure association constant for IL1R-FcV-RAcP-FcII heterodimer and IL-1β/IL-1F2. Anti-human IgG were covalently immobilized on CM5 Sensor Chip then IL1R-FcV-RAcP-FcII heterodimer was loaded and followed by various concentrations of human IL-1β/IL-1F2. Series of sensograms were generated and used for calculation of Kd value.

Figure 2:
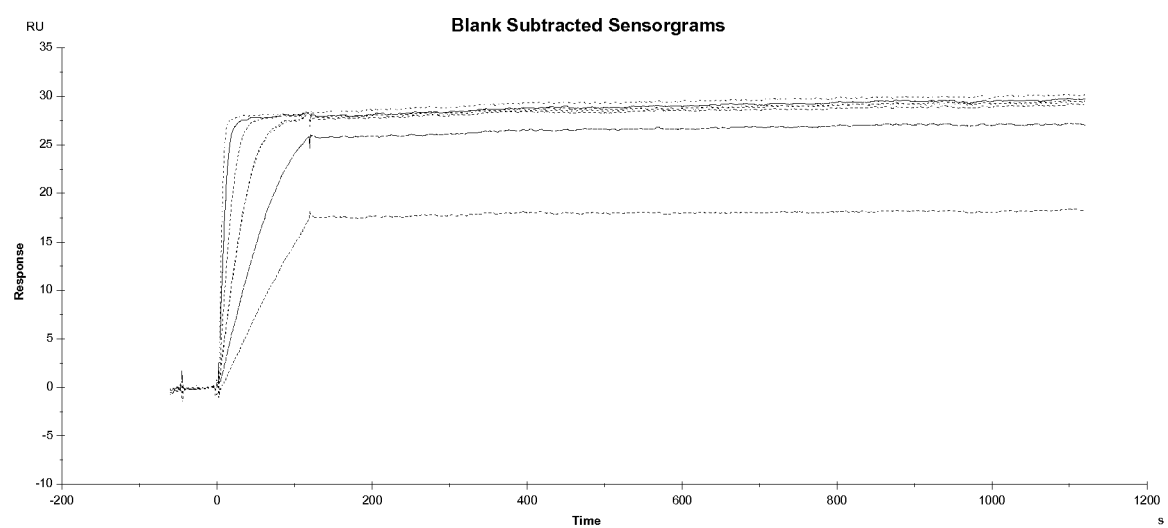
FIG. 2 shows a representative series of buffer-normalized sensograms at various concentrations of IL-1β/IL-1F2, the lowest curve represents IL-1β/IL-1F2 concentration of 0.919 nM and each subsequent curve represents 1.838, 3.676, 7.35, 14.7 and 29.4 nM respectively.

Experimental Setup:
1. In preliminary series of experiments, several different concentrations (1, 10 and 100 μg/ml) of IL1R-FcV-RAcP-FcII heterodimer were prepared and tested for their association with immobilized anti-human IgG. It was found that at 1 μg/ml, IL1R-FcV-RAcP-FcII heterodimer produced sufficient signal within the range of ~100 RU and this concentration was used for the entire assay;
2. Parameters for binding/dissociation cycles were optimized in series of pilot runs and are summarized in Table 1;
3. Human IL-1β/IL-1F2 were used at the concentrations specified in Table 2 where concentration of 3.676 nM was run two time independently as an internal control for the instrument reproducibility;
4. Series of sensograms corresponding to different concentrations IL-1β/IL-1F2 were generated. The data were normalized by subtraction of 'buffer only' sensorgam. The buffer-normalized sensograms are shown in FIG. 2 and corresponding data are presented in Table 2.

TABLE 1

| Parameters of BiaCore cycles | | |
|---|---|---|
| Process | Time, s | Flow rate, μl/min |
| Heterodimer loading | 120 | 10 |
| IL1 loading | 120 | 30 |
| Dissociation | 1000 | 30 |
| Regeneration | 20 | 30 |

Analysis of Experimental Data

Experimental conditions were optimized to enable accurate use of curve fit algorithms. As evident from the sensograms (FIG. 2), all tested concentrations of IL-1β/IL-1F2 displayed dose-dependent association curves. However, due to very high affinity of IL1R-FcV-RAcP-FcII heterodimer/IL-1β/IL-1F2 interaction, there was no detectable dissociation within 1000 s range. Therefore, calculation of Kd values using Kinetic model could not be accurately carried out.

As an alternative way for Kd calculation, Steady-State data analysis using 1:1 Langmuir binding model was used. According to this method, Kd is calculated from series of plots of steady-state analyte binding levels ($R_{eq}$) against concentration. The obtained data are summarized in Table 2.

Figure 3:
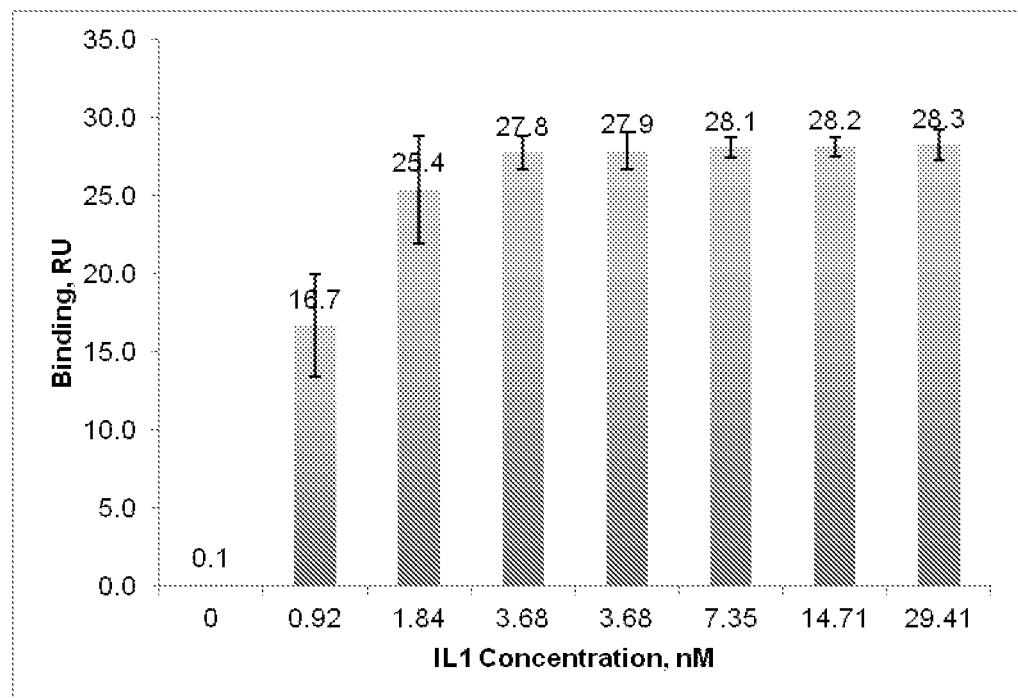
FIG. 3 shows a representative IL1 binding data, relative response was calculated by subtraction of 'buffer only' background, error bars reflect standard deviation values calculated by Bioacore T200 Evaluation Software package.
Figure 4:
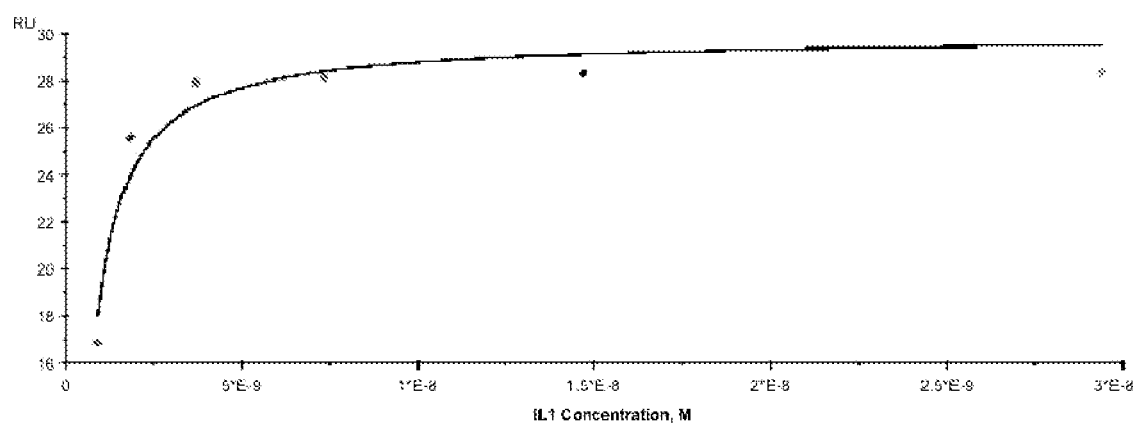
FIG. 4 shows representative 'Response vs. Concentration' curve, concentration of IL-1β/IL-1F2 is shown on the X-axis in Mol and Response in RU (Req) is shown on the Y-axis.

Experimental data are summarized in Table 3 and are shown in FIG. 3. A 4-parameter curve fit algorithm was used and the resulting curve, Response vs. Concentration is shown of FIG. 4. The equation describing this curve was used for Kd calculation and was performed by Biacore T200 Evaluation Software.

TABLE 2

Kd value for IL1R-FcV-RAcP-FcII heterodimer and human IL-1β/IL-1F2 calculated from steady-state model.

| Sample | Kd (M) | Rmax (RU) | Offset (RU) | Chi$^2$ | Chi$^2$/Rmax, % |
|---|---|---|---|---|---|
| IL1 | 9.63E-12 | 1134.263 | 1104.354 | 1.987 | 0.175 |

TABLE 3

IL-1β/IL-1F2 concentrations and binding (Relative Response). Standard Deviation values, %, were calculated by Biacore T200 Evaluation Software and then converted into Standard Deviation by multiplying Rmax*StDev %. The StDev values are plotted as error bars on FIG. 3.

| Cycle # | IL1, nM | Rmax (RU) | StDev, % | StDev |
|---|---|---|---|---|
| 2 | 0 | -0.1 | 0.031 | 0.004 |
| 3 | 0.92 | 16.7 | 0.194 | 3.25 |
| 4 | 1.84 | 25.4 | 0.135 | 3.44 |
| 5 | 3.68 | 27.8 | 0.038 | 1.07 |
| 6 | 3.68 | 27.9 | 0.042 | 1.18 |
| 7 | 7.35 | 28.1 | 0.023 | 0.64 |
| 8 | 14.71 | 28.2 | 0.022 | 0.62 |
| 9 | 29.41 | 28.3 | 0.035 | 1.00 |

Example 3: Pharmacokinetics (PK) of IL1R-FcV-RAcP-FcII Heterodimer after Subcutaneous Administration in Mice Polypeptides of IL1R-FcV-RAcP-FcII heterodimer (SEQ ID NO.1 and SEQ ID NO. 2) were co-expressed and purified essentially as described in the forgoing examples. For administration into animals, the polypeptides were formulated in the following buffer: 1% w/v Sucrose, 100 mM Sodium Chloride, 20 mM L-Arginine Hydrochloride, 25 mM Sodium Bicarbonate, pH 6.3. The dosing stock concentration used was 0.5 mg/mL of the polypeptide.

Fourteen male DBA/1 mice were randomized by body weight into seven groups of two animals on Day 0 of the study. A single dose of IL1R-FcV-RAcP-FcII heterodimer (5 mg/kg in 10 ml/kg) was administered subcutaneously (dorsally) on Day 0 to mice in six of the groups. The mice in the remaining group remained untreated and were bled via cardiac puncture for plasma preparation on Day 0 of the study. Plasma was prepared from blood samples collected from mice in the treated groups via the orbital sinus or terminal cardiac puncture at specified times throughout the study. Body weights were recorded for all animals on the treatment day (Day 0) and then three times per week, including the termination day of each group. Body weight change was not measured in groups culled for sample collection at 0 hours and within 36 hours of dose administration. Mean body weight loss between Day 0 and termination of the groups culled between 96 hours and 21 days post-dose was minimal. No mice lost body weight exceeding ethical limits. Following the in-life phase of the study, plasma samples were analyzed by Enzyme Linked Immunosorbent Assay (ELISA) for Hu-Fc proteins. Quantification of Hu-Fc in mouse plasma samples by ELISA was used as a read-out for circulating levels of IL1R-FcV-RAcP-FcII heterodimer. The assay was performed on samples from all mice in the study.

The polypeptides (detected as Human-Fc protein) were detected in the plasma of animals at all time-points post-dose. One Phase Decay Model equation using Prism 5.0c (GraphPad Software Inc, La Jolla, Calif., USA) was then used to determine pharmacokinetics of the polypeptides as detected by Hu-Fc ELISA. Peak circulating level of Hu-Fc (Cmax) was determined to be 1.284 µg/mL, and time to peak circulating levels (Tmax) was 24 hours post-dose. The half-life (T1/2) was 97 hours, 31 minutes and the rate constant (K) was 0.0071 hr-1. Hu-Fc was below the level of detection in the plasma of the untreated animals. The results of the study are summarized in Table 4.

TABLE 4

Mean Human-Fc Protein Concentration ± SEM (µg/mL) at each Time Post-Administration

| Group | Treatment | Bleeding Schedule (time post-administration) | Mean Human-Fc Protein Concentration [µg/mL] | SEM |
|---|---|---|---|---|
| 1 | No treatment | 0 hours# | <0.040* | 0.000 |
| 2 | polypeptide of | 30 minutes^ | 0.054 | 0.002 |
| 3 | SEQ IDs NO. | 1 hour^ | 0.257 | 0.066 |
| 4 | 1 and NO. 2 (5 | 2 hours^ | 0.247 | 0.045 |
| 5 | mg/kg, Once | 4 hours^ | 0.801 | 0.073 |
| 6 | only, s.c.) | 8 hours^ | 1.156 | 0.070 |
| 7 | | 10 hours^ | 1.252 | 0.007 |
| 2 | | 24 hours# | 1.284 | 0.022 |
| 3 | | 36 hours# | 1.158 | 0.034 |
| 4 | | 96 hours# | 1.145 | 0.052 |
| 5 | | 7 days# | 0.210 | 0.068 |
| 6 | | 14 days# | 0.102 | 0.017 |
| 7 | | 21 days# | 0.117 | 0.032 |

*0.040 is the limit of detection for this assay.
The Human-Fc Protein Concentration was determined by Prism Software based on the mean absorbance of the triplicate samples
^Bleed via orbital sinus
Bleed via terminal cardiac puncture

Figure 5:
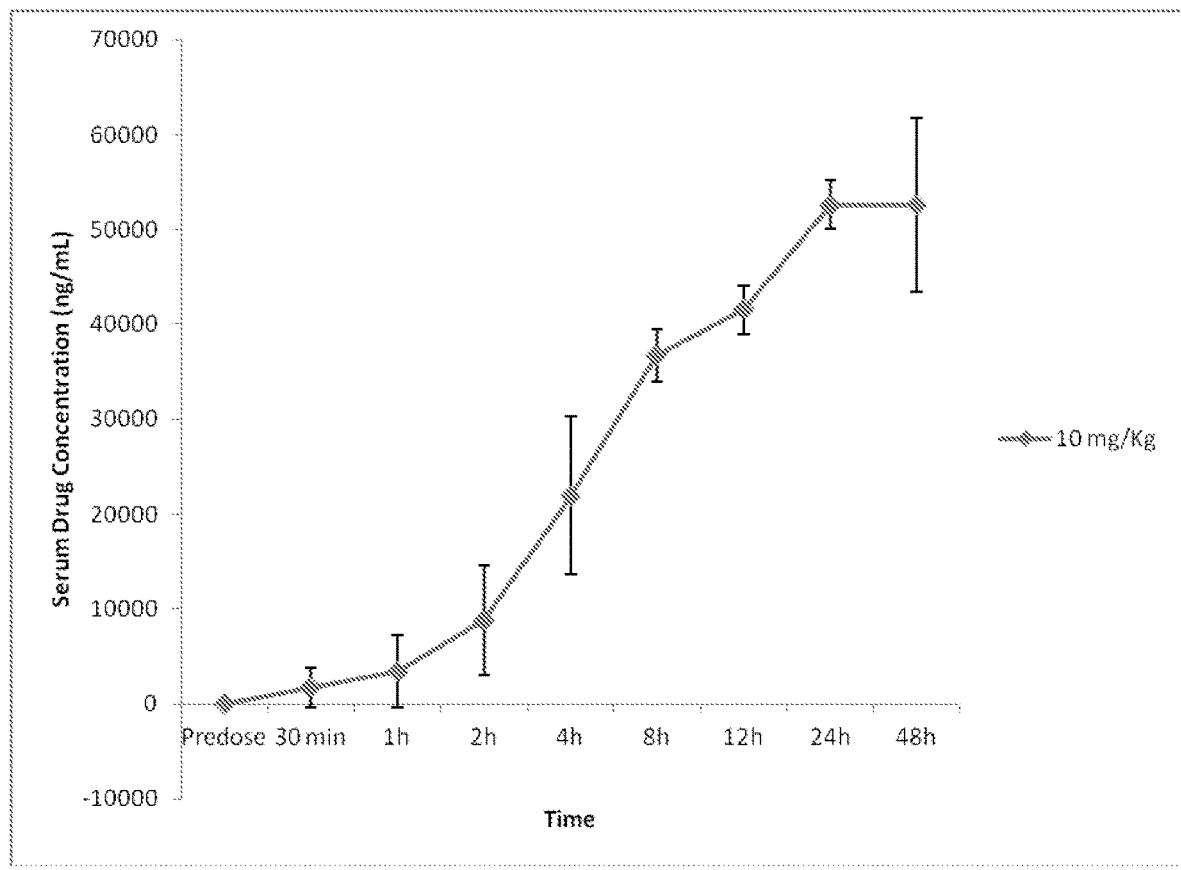
FIG. 5 shows concentration of IL1R-FcV-RAcP-FcII heterodimer (in ng/ml) in the serum of the initial set of three Cynomolgus Monkey after a single subcutaneous administration at a dose of 10 mg/kg (vertical bars represent standard deviation values at various time points)

Example 4: Pharmacokinetics (PK) of IL1R-FcV-RAcP-FcII Heterodimer after Subcutaneous Administration in Primates For the purpose of this study, initially three naïve male Cynomolgus monkeys were used. The animals were approximately 2-4 years old and weighed approximately 2 kg. The animals received a single dose of IL1R-FcV-RAcP-FcII heterodimer (SEQ ID NO. 1 and SEQ ID NO. 2), formulated essentially as described in the foregoing Example 1, by subcutaneous administration at a dose level of 10 mg/kg on Day 1 of the study. The results of the bioanalysis from the initial set of three animals are shown in FIG. 5. To further meet the study objectives, an additional 3 male Cynomolgus monkeys received a single dose of IL1R-FcV-RAcP-FcII heterodimer by subcutaneous administration on Day 1 at a dose level of 10 mg/kg and blood samples were collected at designated time points until Day 21. The results of the bioanalysis from the follow-up additional set of three animals are shown in FIG. 5. All the animals were observed once daily for any reactions to treatment during the study. Body weights were measured and recorded prior to dosing. Blood samples for pharmacokinetic analysis were collected at the designated time points. The collected serum samples were stored at −80° C. for bioanalysis. The determination of plasma concentrations of the polypeptides were performed using the ELISA method described in the foregoing Example 3.

There were no clinical signs noted during the course of the study. Body weight profiles were considered satisfactory. Results from the initial PK data analysis showed the Cmax and Tmax following single subcutaneous administration at 10 mg/kg were to be approximately 24-48 h. PK results from the additional 3 animals showed, the IL1R-FcV-RAcP-FcII heterodimer was quantifiable in plasma until at least 10 days for 2 of the 3 animals, and up to day 14 for one animal. The pharmacokinetics parameters for the follow-up set of three monkeys were determined using a non-compartmental model in WinNonLin 6.3 software package and are summarized in Table 5.

TABLE 5

Summary of PK parameters for a single subcutaneous dose administration study in Cynomolgus monkeys (values in parenthesis are mean CV %)

| Dose | $t_{1/2}^1$ (day) | $t_{max}^2$ (day) | $C_{max}$ (µg/mL) | $AUC_{0-t}$ (µg · day/ml) | $AUC_{0-7}$ (µg · day/ml) |
|---|---|---|---|---|---|
| 10 mg/kg | 4.03 * | 2.00 [1.00-2.00] | 39.8 (61.0) | 272 (65.3) | 210 (62.3) |

[1] harmonic mean
[2] median [min-max]
* estimated value since AUCextra > 20%

Figure 6:
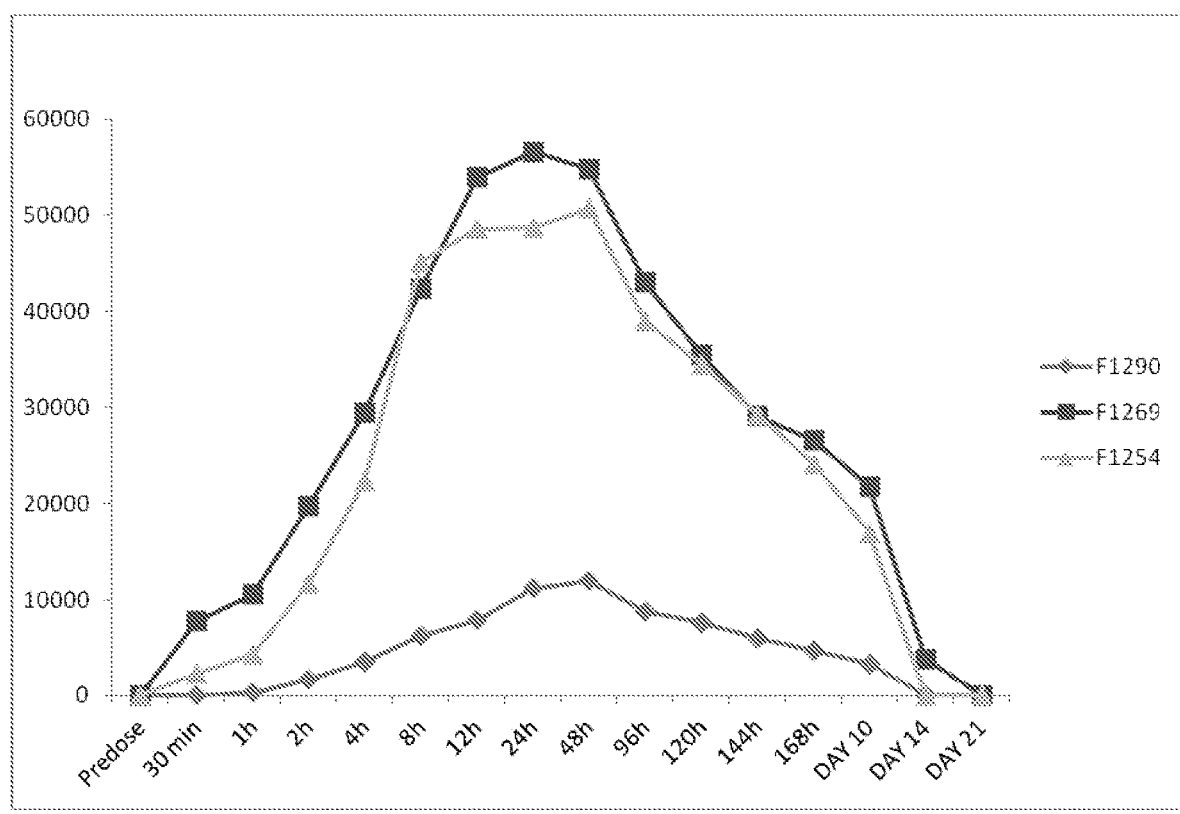
FIG. 6 shows concentration of IL1R-FcV-RAcP-FcII heterodimer (in ng/ml) in the serum of the follow-up set of three Cynomolgus Monkey after a single subcutaneous administration at a dose of 10 mg/kg, the three curves shown represent measurements taken from three individual animals designated F1290, F1269 and F1254.

All animals were widely exposed to IL1R-FcV-RAcP-FcII heterodimer. The observed inter-individual variability was relatively high with a CV % of about 60%. The latter was explained by the lowest drug exposure found in animal F1290 (FIG. 6), which was at least 5-fold less exposed to IL1R-FcV-RAcP-FcII heterodimer than the remaining two animals. The maximal concentration (Cmax) was reached between 1st and 2nd days. The estimated T1/2 was evaluated to be about 4 days.

Example 5: Interspecies Specific Activity of IL1R-FcV-RAcP-FcII Heterodimer

IL1R-FcV-RAcP-FcII is a heterodimer comprised of soluble portions of human IL-1R and IL-1RAcP each linked to a unique IgG1 Fc portion. Sequence alignment of the 333 amino acid portion of the human IL-1R with relevant portions from several species demonstrates only a modest sequence identity (~64%) with IL-1R portions from rodents (mouse, rat). However, the sequence identity is much higher between human IL-1R and those of other primates (e.g. 91% with marmoset monkey). Further presented below are protein binary sequence alignments of the 358 amino acid portion of the human IL-1RAcP, forming a part of IL1R-FcV-RAcP-FcII heterodimer molecule, with relevant portions from several species. Cross-species sequence identity of this portion of IL1R-FcV-RAcP-FcII heterodimer is somewhat higher. Higher sequence identity is also observed comparing the 358 amino acid portion of the human IL-1RAcP with its ortholog from *Macaca mulatta* (92%) vs comparing with the ortholog from *Mus musculus* (85%).

In order to comparatively evaluate the functional (inhibitory) properties of a novel drug candidate IL1R-FcV-RAcP-FcII heterodimer (SEQ ID NO. 1 and SEQ ID NO. 2) the following study was performed. Assays were carried out using human, *Macaca* Rhesus and murine IL-1β IL-1F2 orthologs. Human vs. Mouse IL-1β/IL-1F2 were compared in Mouse Embryo Fibroblasts. Human vs. M. Rhesus IL-1β IL-1F2 were compared in MRC5 human lung fibroblasts. As a functional comparator, previously characterized mouse monoclonal antibodies against human IL-1β IL-1F2 and goat polyclonal antibodies against mouse IL-1β IL-1F2 were used. Quantification of IL-1β IL-1F2-induced IL-6 production by MRC5 cells or MEFs was used for determination of inhibitory properties (IC50 values) for all three orthologs.

Figure 7:
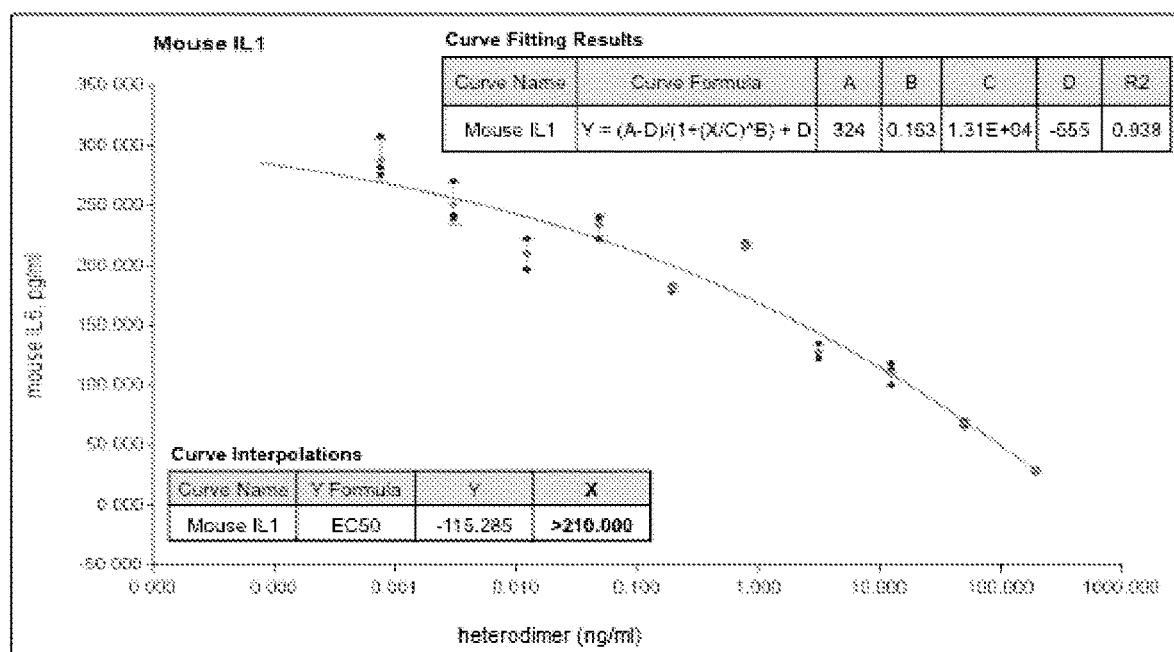
FIG. 7 shows IL1R-FcV-RAcP-FcII heterodimer titration curve of mouse IL6 secretion induced by mouse IL-1B/IL-1F2 in MEFs, the insert table shows curve fitting results using 4-parameter algorithm and curve interpolation for determination of the IC50 value.
Figure 8:
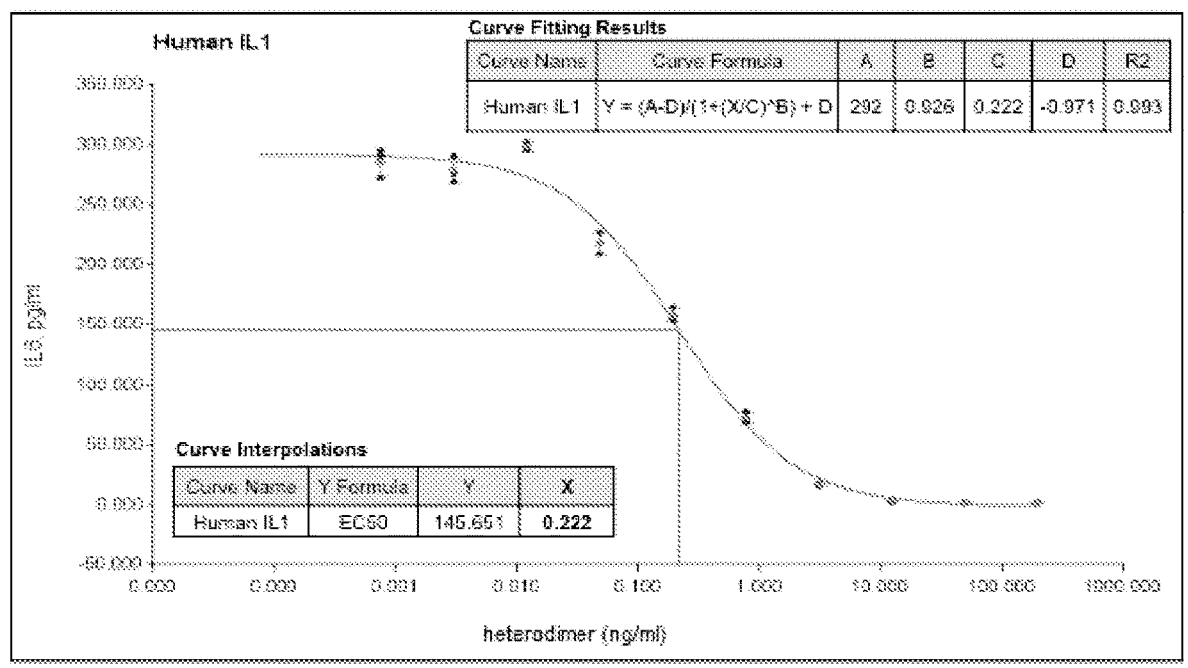
FIG. 8 shows IL1R-FcV-RAcP-FcII heterodimer titration curve of human IL6 secretion induced by human IL-1B/IL-1F2 in MRC5 cells, the insert table shows curve fitting results using 4-parameter algorithm and curve interpolation for determination of the IC50 value.
Figure 9:
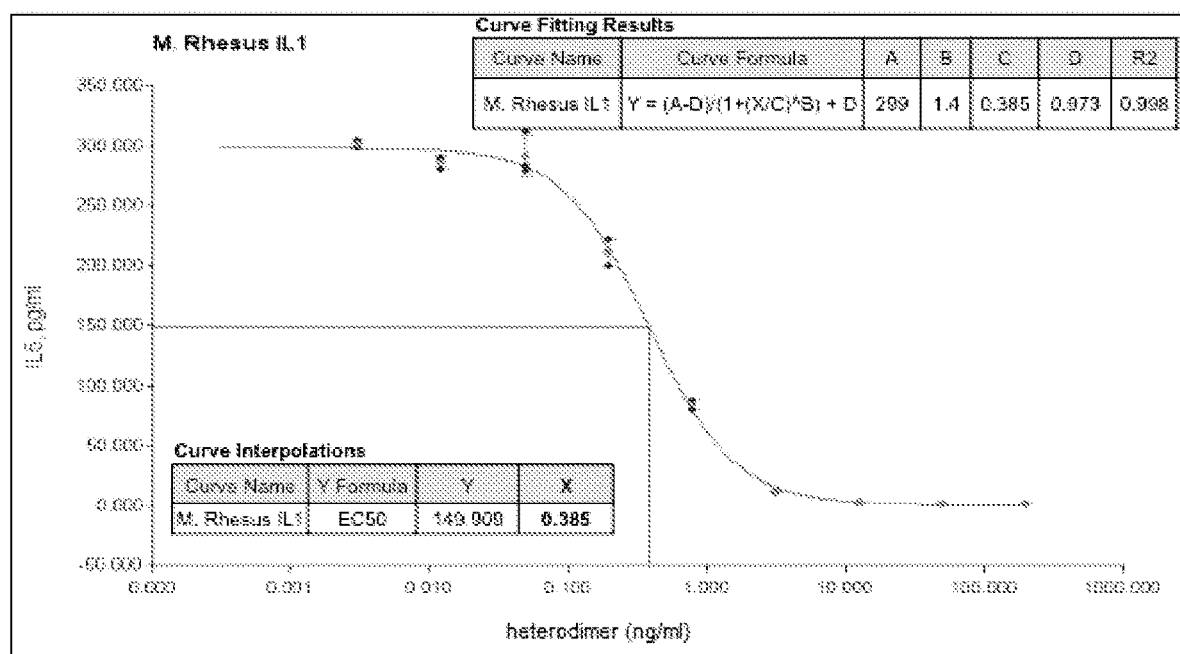
FIG. 9 shows IL1R-FcV-RAcP-FcII heterodimer titration curve of human IL6 secretion induced by M. Rhesus IL-1B/IL-1F2 in MRC5 cells, the insert table shows curve fitting results using 4-parameter algorithm and curve interpolation for determination of the IC50 value.

Materials and Reagents
Cells
MRC5 cells, Human Lung Fibroblasts, ATCC Cat # CCL-171, Lot #59474707.
Mouse Embryo Fibroblasts (MEFs) used for the experiments.
Medium
DMEM, Dulbecco's Modification of Eagle's Medium, high glucose (4.5 g/L), Invitrogen, Cat #11995-065, Lot #1237317, supplemented with L-glutamine and 1× penn/strep and 10% Benchmark Fetal Bovine Serum, Gemini Bioproducts, Cat #100-106, Lot # A78D00E.
Reagents
IL1R-FcV-RAcP-FcII heterodimer, Preparation of 1.5 mg/ml.
IL-1β IL-1F2, Human recombinant, *E. coli*-derived, Ala117-Ser269, Accession #NP_000567, R&D systems, Cat #201-LB, Lot # AD1412111
IL-1β IL-1F2, M. Rhesus recombinant, *E. coli*-derived, Ala117-Ser269, Accession # P48090, R&D systems, Cat #1318-RL, Lot # GUG0110111
IL-1β/IL-1F2, Mouse recombinant, *E. coli*-derived, Vla118-Ser269, Accession #NP_032387, R&D systems, Cat #401-ML-005, Lot # BN0713032
Mouse monoclonal antibodies against human IL-1β/IL-1F2, clone #8516, R&D systems, Cat # MAB201, Lot # AWE1011081
Goat polyclonal antibodies against mouse IL-1β/IL-1F2, clone #8516, R&D systems, Cat #AF-401-NA, Lot # NP2812121
IL-6 Quantakine Immunoassay, R&D systems, Cat # D6050, Lot #308916
Mouse IL-6 Quantakine Immunoassay, R&D systems, Cat # M6000B, Lot #309487
Procedure
Cell Maintenance
Centrifuge the supernatants at 300×g for 10 min, collect cleared supernatants and use them for ELISA either directly (MEFs) or with 1/5 dilution (MRC5) if appropriate according to pilot experiments.
ELISA
This assay employs the quantitative sandwich enzyme immunoassay technique. A monoclonal antibody specific for IL-6 has been pre-coated onto a microplate. Standards and samples are pipetted into the wells and any IL-6 present is bound by the immobilized antibody. After washing away any unbound substances, an enzyme-linked polyclonal antibody specific for IL-6 is added to the wells. Following a wash to remove any unbound antibody-enzyme reagent, a substrate solution is added to the wells and color develops in proportion to the amount of IL-6 bound in the initial step. The color development is stopped and the intensity of the color is measured.
Experimental Data
The goal of three series of experiments was to identify suitable cell line for measuring IL6 secretion upon treatment with human and mouse orthologs of IL-1β/IL-1F2. Several preliminary pilot experiments were carried out to identify mouse cells that respond to mouse-IL-1β/IL-1F2 treatment by robust secretion of IL6. On the basis of these preliminary experiments, MEFs were chosen as a model cell line for IL1R-FcV-RAcP-FcII heterodimer titration experiments. IL1R-FcV-RAcP-FcII heterodimer titration curve of mouse IL6 secretion induced by mouse IL-1B/IL-1F2 in MEFs is shown in FIG. 7. The IL6 production data were calculated from the calibration curve shown on FIG. 9. The insert table shows curve fitting results using 4-parameter algorithm and curve interpolation for determination of the IC50 value. The calculated IL1R-FcV-RAcP-FcII heterodimer IC50 value for mouse IL-1B/IL-1F2 is >210 ng/ml.

The experimental data indicates that IL1R-FcV-RAcP-FcII heterodimer is an efficient inhibitor of human IL-1β/IL-1F2, but not mouse IL-1B/IL-1F2 signaling pathway: IL1R-FcV-RAcP-FcII heterodimer IC50 value for human IL-1B/IL-1F2 is 0.19 ng/ml and for mouse IL-1B/IL-1F2->200 ng/ml (0.95 pM and >1000 pM respectively, assuming molecular mass of IL1R-FcV-RAcP-FcII heterodimer as 200 kDa). IL1R-FcV-RAcP-FcII heterodimer titration curve of human IL6 secretion induced by human IL-1B/IL-1F2 in MRC5 cells is shown in FIG. 8. The calculated IC50 value of IL1R-FcV-RAcP-FcII heterodimer against human IL-1B/IL-1F2 (X-column in the Curve Interpolation table) is 0.22 ng/mL. IL1R-FcV-RAcP-FcII heterodimer titration curve of human IL6 secretion induced by M. Rhesus IL-1B/IL-1F2 in MRC5 cells is shown in FIG. 9. The calculated IL1R-FcV-RAcP-FcII heterodimer IC50 value for human IL-1B/IL-1F2 is 0.38 ng/ml. IL-6 recovery from IL1R-FcV-RAcP-FcII heterodimer preparation with a final concentration of 200 ng/ml was 95%. IL1R-FcV-RAcP-FcII heterodimer is an efficient inhibitor of both human and M. Rhesus IL-1B/IL-1F2 signaling pathway: IL1R-FcV-RAcP-FcII heterodimer IC50 value for human IL-1B/IL-1F2 is 0.19 ng/ml and for M. Rhesus IL-1B/IL-1F2-0.38 ng/ml (1.1 pM and 1.9 pM, respectively). IL-6 recovery from IL1R-FcV-RAcP-FcII heterodimer preparation with a final concentration of 200 ng/ml was 92%.

Thus, stimulation of IL-6 production upon treatment of mouse or human cells with IL-1B/IL-1F2 was used a functional test for inhibitory properties of a novel drug candidate IL1R-FcV-RAcP-FcII heterodimer against human, mouse and M. Rhesus orthologs of IL-1B/IL-1F2. Suitable cell lines were identified and experimental conditions including cell density, treatment duration linear range for IL6 detection and were optimized for all three orthologs. The obtained data are summarized in Table 6.

TABLE 6

IC50 values for IL1R-FcV-RAcP-FcII heterodimer against human, mouse and M. Rhesus orthologs of IL-1B/IL-1F2.

| IL-1β/IL-1F2 | Cells | IC50, ng/ml | IC50, pM |
|---|---|---|---|
| Human | MEFs | 0.19 | 0.95 |
| Human | MRC5 | 0.22 | 1.1 |
| Mouse | MEFs | >210 | >1,050 |
| M. Rhesus | MRC5 | 0.38 | 1.9 |

All publications and patents mentioned herein are hereby incorporated by reference in their entirety as if each individual publication or patent was specifically and individually indicated to be incorporated by reference.

While specific embodiments of the subject matter have been discussed, the above specification is illustrative and not restrictive. Many variations will become apparent to those skilled in the art upon review of this specification and the claims below. The full scope of the invention should be determined by reference to the claims, along with their full scope of equivalents, and the specification, along with such variations.

What is claimed is:

1. A heterodimeric protein composition capable of binding human IL-1β, said protein composition comprising a first polypeptide comprising amino acid sequence of SEQ ID NO. 1 and a second polypeptide comprising amino acid sequence of SEQ ID NO. 2.

2. The therapeutic composition of claim 1, further comprising about 6% (m/v) sucrose, about 3% (m/v) polyethylene glycol having an average molecular weight of 3350 Da, about 50 mM sodium chloride, and about 20 mM L-Histidine pH 6.5.

* * * * *

```
                         SEQUENCE LISTING

<160> NUMBER OF SEQ ID NOS: 7

<210> SEQ ID NO 1
<211> LENGTH: 548
<212> TYPE: PRT
<213> ORGANISM: Homo sapiens

<400> SEQUENCE: 1

Leu Glu Ala Asp Lys Cys Lys Glu Arg Glu Glu Lys Ile Ile Leu Val
1               5                   10                  15

Ser Ser Ala Asn Glu Ile Asp Val Arg Pro Cys Pro Leu Asn Pro Asn
            20                  25                  30

Glu His Lys Gly Thr Ile Thr Trp Tyr Lys Asp Asp Ser Lys Thr Pro
        35                  40                  45

Val Ser Thr Glu Gln Ala Ser Arg Ile His Gln His Lys Glu Lys Leu
    50                  55                  60

Trp Phe Val Pro Ala Lys Val Glu Asp Ser Gly His Tyr Tyr Cys Val
65                  70                  75                  80

Val Arg Asn Ser Ser Tyr Cys Leu Arg Ile Lys Ile Ser Ala Lys Phe
                85                  90                  95

Val Glu Asn Glu Pro Asn Leu Cys Tyr Asn Ala Gln Ala Ile Phe Lys
            100                 105                 110

Gln Lys Leu Pro Val Ala Gly Asp Gly Gly Leu Val Cys Pro Tyr Met
        115                 120                 125

Glu Phe Phe Lys Asn Glu Asn Asn Glu Leu Pro Lys Leu Gln Trp Tyr
    130                 135                 140

Lys Asp Cys Lys Pro Leu Leu Leu Asp Asn Ile His Phe Ser Gly Val
145                 150                 155                 160
```

```
Lys Asp Arg Leu Ile Val Met Asn Val Ala Glu Lys His Arg Gly Asn
            165                 170                 175

Tyr Thr Cys His Ala Ser Tyr Thr Tyr Leu Gly Lys Gln Tyr Pro Ile
            180                 185                 190

Thr Arg Val Ile Glu Phe Ile Thr Leu Glu Glu Asn Lys Pro Thr Arg
            195                 200                 205

Pro Val Ile Val Ser Pro Ala Asn Glu Thr Met Glu Val Asp Leu Gly
            210                 215                 220

Ser Gln Ile Gln Leu Ile Cys Asn Val Thr Gly Gln Leu Ser Asp Ile
225                 230                 235                 240

Ala Tyr Trp Lys Trp Asn Gly Ser Val Ile Asp Glu Asp Pro Val
            245                 250                 255

Leu Gly Glu Asp Tyr Tyr Ser Val Glu Asn Pro Ala Asn Lys Arg Arg
            260                 265                 270

Ser Thr Leu Ile Thr Val Leu Asn Ile Ser Glu Ile Glu Ser Arg Phe
            275                 280                 285

Tyr Lys His Pro Phe Thr Cys Phe Ala Lys Asn Thr His Gly Ile Asp
            290                 295                 300

Ala Ala Tyr Ile Gln Leu Ile Tyr Pro Val Thr Asn Gly Ser Gly Gly
305                 310                 315                 320

Gly Asp Lys Thr His Thr Cys Pro Pro Cys Pro Ala Pro Glu Leu Leu
            325                 330                 335

Gly Gly Pro Ser Val Phe Leu Phe Pro Pro Lys Pro Lys Asp Thr Leu
            340                 345                 350

Met Ile Ser Arg Thr Pro Glu Val Thr Cys Val Val Val Asp Val Ser
            355                 360                 365

His Glu Asp Pro Glu Val Lys Phe Asn Trp Tyr Val Asp Gly Val Glu
            370                 375                 380

Val His Asn Ala Lys Thr Lys Pro Arg Glu Glu Gln Tyr Asn Ser Thr
385                 390                 395                 400

Tyr Arg Val Val Ser Val Leu Thr Val Leu His Gln Asp Trp Leu Asn
            405                 410                 415

Gly Lys Glu Tyr Lys Cys Lys Val Ser Asn Lys Ala Leu Pro Ala Pro
            420                 425                 430

Ile Glu Lys Thr Ile Ser Lys Ala Lys Gly Gln Pro Arg Glu Pro Gln
            435                 440                 445

Val Cys Thr Leu Pro Pro Ser Arg Asp Glu Leu Thr Lys Asn Gln Val
            450                 455                 460

Ser Leu Ser Cys Ala Val Lys Gly Phe Tyr Pro Ser Asp Ile Ala Val
465                 470                 475                 480

Glu Trp Glu Ser Asn Gly Gln Pro Glu Asn Asn Tyr Lys Thr Thr Pro
            485                 490                 495

Pro Val Leu Asp Ser Asp Gly Ser Phe Lys Leu Val Ser Lys Leu Thr
            500                 505                 510

Val Asp Lys Ser Arg Trp Gln Gln Gly Asn Val Phe Ser Cys Ser Val
            515                 520                 525

Met His Glu Ala Leu His Asn His Tyr Thr Gln Lys Ser Leu Ser Leu
530                 535                 540

Ser Pro Gly Lys
545

<210> SEQ ID NO 2
<211> LENGTH: 570
```

```
<212> TYPE: PRT
<213> ORGANISM: Homo sapiens

<400> SEQUENCE: 2

Ser Glu Arg Cys Asp Asp Trp Gly Leu Asp Thr Met Arg Gln Ile Gln
1               5                   10                  15

Val Phe Glu Asp Glu Pro Ala Arg Ile Lys Cys Pro Leu Phe Glu His
            20                  25                  30

Phe Leu Lys Phe Asn Tyr Ser Thr Ala His Ser Ala Gly Leu Thr Leu
        35                  40                  45

Ile Trp Tyr Trp Thr Arg Gln Asp Arg Asp Leu Glu Glu Pro Ile Asn
50                  55                  60

Phe Arg Leu Pro Glu Asn Arg Ile Ser Lys Glu Lys Asp Val Leu Trp
65                  70                  75                  80

Phe Arg Pro Thr Leu Leu Asn Asp Thr Gly Asn Tyr Thr Cys Met Leu
                85                  90                  95

Arg Asn Thr Thr Tyr Cys Ser Lys Val Ala Phe Pro Leu Glu Val Val
            100                 105                 110

Gln Lys Asp Ser Cys Phe Asn Ser Pro Met Lys Leu Pro Val His Lys
        115                 120                 125

Leu Tyr Ile Glu Tyr Gly Ile Gln Arg Ile Thr Cys Pro Asn Val Asp
130                 135                 140

Gly Tyr Phe Pro Ser Ser Val Lys Pro Thr Ile Thr Trp Tyr Met Gly
145                 150                 155                 160

Cys Tyr Lys Ile Gln Asn Phe Asn Asn Val Ile Pro Glu Gly Met Asn
                165                 170                 175

Leu Ser Phe Leu Ile Ala Leu Ile Ser Asn Asn Gly Asn Tyr Thr Cys
            180                 185                 190

Val Val Thr Tyr Pro Glu Asn Gly Arg Thr Phe His Leu Thr Arg Thr
        195                 200                 205

Leu Thr Val Lys Val Val Gly Ser Pro Lys Asn Ala Val Pro Pro Val
210                 215                 220

Ile His Ser Pro Asn Asp His Val Val Tyr Glu Lys Glu Pro Gly Glu
225                 230                 235                 240

Glu Leu Leu Ile Pro Cys Thr Val Tyr Phe Ser Phe Leu Met Asp Ser
                245                 250                 255

Arg Asn Glu Val Trp Trp Thr Ile Asp Gly Lys Lys Pro Asp Asp Ile
            260                 265                 270

Thr Ile Asp Val Thr Ile Asn Glu Ser Ile Ser His Ser Arg Thr Glu
        275                 280                 285

Asp Glu Thr Arg Thr Gln Ile Leu Ser Ile Lys Lys Val Thr Ser Glu
290                 295                 300

Asp Leu Lys Arg Ser Tyr Val Cys His Ala Arg Ser Ala Lys Gly Glu
305                 310                 315                 320

Val Ala Lys Ala Ala Lys Val Lys Gln Lys Val Pro Ala Pro Arg Tyr
                325                 330                 335

Thr Val Gly Ser Gly Gly Gly Asp Lys Thr His Thr Cys Pro Pro Cys
            340                 345                 350

Pro Ala Pro Glu Leu Leu Gly Gly Pro Ser Val Phe Leu Phe Pro Pro
        355                 360                 365

Lys Pro Lys Asp Thr Leu Met Ile Ser Arg Thr Pro Glu Val Thr Cys
370                 375                 380

Val Val Val Asp Val Ser His Glu Asp Pro Glu Val Lys Phe Asn Trp
385                 390                 395                 400
```

Tyr Val Asp Gly Val Glu Val His Asn Ala Lys Thr Lys Pro Arg Glu
            405                 410                 415

Glu Gln Tyr Asn Ser Thr Tyr Arg Val Val Ser Val Leu Thr Val Leu
        420                 425                 430

His Gln Asp Trp Leu Asn Gly Lys Glu Tyr Lys Cys Lys Val Ser Asn
            435                 440                 445

Lys Ala Leu Pro Ala Pro Ile Glu Lys Thr Ile Ser Lys Ala Lys Gly
450                 455                 460

Gln Pro Arg Glu Pro Gln Val Tyr Thr Leu Pro Pro Cys Arg Asp Glu
465                 470                 475                 480

Leu Thr Lys Asn Gln Val Ser Leu Trp Cys Leu Val Lys Gly Phe Tyr
            485                 490                 495

Pro Ser Asp Ile Ala Val Glu Trp Glu Ser Asn Gly Gln Pro Glu Asn
            500                 505                 510

Asn Tyr Lys Thr Thr Pro Pro Val Leu Asp Ser Asp Gly Ser Phe Phe
        515                 520                 525

Leu Tyr Ser Ala Leu Thr Val Asp Lys Ser Arg Trp Gln Gln Gly Asn
        530                 535                 540

Val Phe Ser Cys Ser Val Met His Glu Ala Leu His Asn His Tyr Thr
545                 550                 555                 560

Gln Lys Ser Leu Ser Leu Ser Pro Gly Lys
            565                 570

<210> SEQ ID NO 3
<211> LENGTH: 565
<212> TYPE: PRT
<213> ORGANISM: Homo sapiens

<400> SEQUENCE: 3

Met Lys Val Leu Leu Arg Leu Ile Cys Phe Ile Ala Leu Leu Ile Ser
1               5                   10                  15

Ser Leu Glu Ala Asp Lys Cys Lys Glu Arg Glu Glu Lys Ile Ile Leu
            20                  25                  30

Val Ser Ser Ala Asn Glu Ile Asp Val Arg Pro Cys Pro Leu Asn Pro
        35                  40                  45

Asn Glu His Lys Gly Thr Ile Thr Trp Tyr Lys Asp Asp Ser Lys Thr
    50                  55                  60

Pro Val Ser Thr Glu Gln Ala Ser Arg Ile His Gln His Lys Glu Lys
65                  70                  75                  80

Leu Trp Phe Val Pro Ala Lys Val Glu Asp Ser Gly His Tyr Tyr Cys
                85                  90                  95

Val Val Arg Asn Ser Ser Tyr Cys Leu Arg Ile Lys Ile Ser Ala Lys
            100                 105                 110

Phe Val Glu Asn Glu Pro Asn Leu Cys Tyr Asn Ala Gln Ala Ile Phe
        115                 120                 125

Lys Gln Lys Leu Pro Val Ala Gly Asp Gly Gly Leu Val Cys Pro Tyr
130                 135                 140

Met Glu Phe Phe Lys Asn Glu Asn Asn Glu Leu Pro Lys Leu Gln Trp
145                 150                 155                 160

Tyr Lys Asp Cys Lys Pro Leu Leu Leu Asp Asn Ile His Phe Ser Gly
                165                 170                 175

Val Lys Asp Arg Leu Ile Val Met Asn Val Ala Glu Lys His Arg Gly
            180                 185                 190

Asn Tyr Thr Cys His Ala Ser Tyr Thr Tyr Leu Gly Lys Gln Tyr Pro

```
                195                 200                 205
Ile Thr Arg Val Ile Glu Phe Ile Thr Leu Glu Glu Asn Lys Pro Thr
210                 215                 220

Arg Pro Val Ile Val Ser Pro Ala Asn Glu Thr Met Glu Val Asp Leu
225                 230                 235                 240

Gly Ser Gln Ile Gln Leu Ile Cys Asn Val Thr Gly Gln Leu Ser Asp
                245                 250                 255

Ile Ala Tyr Trp Lys Trp Asn Gly Ser Val Ile Asp Glu Asp Asp Pro
            260                 265                 270

Val Leu Gly Glu Asp Tyr Tyr Ser Val Glu Asn Pro Ala Asn Lys Arg
        275                 280                 285

Arg Ser Thr Leu Ile Thr Val Leu Asn Ile Ser Glu Ile Glu Ser Arg
    290                 295                 300

Phe Tyr Lys His Pro Phe Thr Cys Phe Ala Lys Asn Thr His Gly Ile
305                 310                 315                 320

Asp Ala Ala Tyr Ile Gln Leu Ile Tyr Pro Val Thr Asn Gly Ser Gly
                325                 330                 335

Gly Gly Asp Lys Thr His Thr Cys Pro Pro Cys Pro Ala Pro Glu Leu
            340                 345                 350

Leu Gly Gly Pro Ser Val Phe Leu Phe Pro Pro Lys Pro Lys Asp Thr
        355                 360                 365

Leu Met Ile Ser Arg Thr Pro Glu Val Thr Cys Val Val Val Asp Val
370                 375                 380

Ser His Glu Asp Pro Glu Val Lys Phe Asn Trp Tyr Val Asp Gly Val
385                 390                 395                 400

Glu Val His Asn Ala Lys Thr Lys Pro Arg Glu Glu Gln Tyr Asn Ser
                405                 410                 415

Thr Tyr Arg Val Val Ser Val Leu Thr Val Leu His Gln Asp Trp Leu
            420                 425                 430

Asn Gly Lys Glu Tyr Lys Cys Lys Val Ser Asn Lys Ala Leu Pro Ala
        435                 440                 445

Pro Ile Glu Lys Thr Ile Ser Lys Ala Lys Gly Gln Pro Arg Glu Pro
    450                 455                 460

Gln Val Cys Thr Leu Pro Pro Ser Arg Asp Glu Leu Thr Lys Asn Gln
465                 470                 475                 480

Val Ser Leu Ser Cys Ala Val Lys Gly Phe Tyr Pro Ser Asp Ile Ala
                485                 490                 495

Val Glu Trp Glu Ser Asn Gly Gln Pro Glu Asn Asn Tyr Lys Thr Thr
            500                 505                 510

Pro Pro Val Leu Asp Ser Asp Gly Ser Phe Lys Leu Val Ser Lys Leu
        515                 520                 525

Thr Val Asp Lys Ser Arg Trp Gln Gln Gly Asn Val Phe Ser Cys Ser
    530                 535                 540

Val Met His Glu Ala Leu His Asn His Tyr Thr Gln Lys Ser Leu Ser
545                 550                 555                 560

Leu Ser Pro Gly Lys
                565

<210> SEQ ID NO 4
<211> LENGTH: 1695
<212> TYPE: DNA
<213> ORGANISM: Homo sapiens

<400> SEQUENCE: 4
```

| | | |
|---|---|---|
| atgaaggtcc tgctcaggct gatctgcttc attgccctgc tcatcagcag cctggaagcc | 60 | |
| gacaagtgca aggagaggga ggagaagatc atcctcgtca gctccgccaa cgagattgat | 120 | |
| gtcaggccct gccccctcaa ccccaatgag cacaagggca caatcacctg gtacaaggac | 180 | |
| gacagcaaga cccctgtctc caccgagcag gccagcagaa tccaccagca caaagagaag | 240 | |
| ctgtggttcg tgcctgccaa ggtggaagac agcggccact actactgtgt ggtgaggaac | 300 | |
| agctcctact gcctcaggat caagatctcc gccaagttcg tggagaacga gcccaacctc | 360 | |
| tgttacaacg ctcaggctat tttcaagcaa aagctccccg tggctggaga cggaggcctg | 420 | |
| gtctgtccct acatggagtt cttcaagaat gagaataatg agctccccaa gctccagtgg | 480 | |
| tacaaggact gtaagcctct gctcctggac aacatccact tctccggcgt gaaggacaga | 540 | |
| ctgatcgtca tgaacgtggc cgagaagcac aggggaaact acacctgtca cgcctcctac | 600 | |
| acctacctcg gcaagcaata tcccatcacc agggtcatcg agttcatcac cctcgaagag | 660 | |
| aacaagccca aaggcctgt catcgtcagc cccgccaatg aaaccatgga ggtggacctc | 720 | |
| ggcagccaga tccagctgat ctgcaacgtg acaggccagc tcagcgacat tgcctactgg | 780 | |
| aagtggaacg gctccgtgat cgacgaagat gatcccgtgc tgggcgagga ctactatagc | 840 | |
| gtggagaacc ccgccaacaa agaaggagc ccctgatca ccgtgctgaa catcagcgag | 900 | |
| atcgagtcca gattctataa gcatcctttc acctgctttg ccaagaacac ccacggcatc | 960 | |
| gacgccgctt acatccagct gatctatccc gtgaccaacg atccggtgg aggtgacaaa | 1020 | |
| actcacacat gcccaccgtg cccagctccg gaactcctgg gcggaccgtc agtcttcctc | 1080 | |
| ttccccccaa aacccaagga caccctcatg atctcccgga cccctgaggt cacatgcgtg | 1140 | |
| gtggtggacg tgagccacga agaccctgag gtcaagttca actggtacgt ggacggcgtg | 1200 | |
| gaggtgcata atgccaagac aaagccgcgg gaggagcagt acaacagcac gtaccgtgtg | 1260 | |
| gtcagcgtcc tcaccgtcct gcaccaggac tggctgaatg gcaaggagta caagtgcaag | 1320 | |
| gtctccaaca aagccctccc agccccatc gagaaaacca tctccaaagc caagggcag | 1380 | |
| ccccgagaac acaggtgtg taccctgccc ccatcccggg atgagctgac caagaaccag | 1440 | |
| gtcagcctga gttgcgcggt caaaggcttc tatcccagcg acatcgccgt ggagtgggag | 1500 | |
| agcaatgggc agccggagaa caactacaag accacgcctc ccgtgttgga ctccgacggc | 1560 | |
| tccttcaagc tcgtcagcaa gctcaccgtg gacaagagca ggtggcagca ggggaacgtc | 1620 | |
| ttctcatgct ccgtgatgca tgaggctctg cacaaccact acacgcagaa gagcctctcc | 1680 | |
| ctgtctccgg gtaaa | 1695 | |

<210> SEQ ID NO 5
<211> LENGTH: 590
<212> TYPE: PRT
<213> ORGANISM: Homo sapiens

<400> SEQUENCE: 5

Met Thr Leu Leu Trp Cys Val Val Ser Leu Tyr Phe Tyr Gly Ile Leu
1               5                   10                  15

Gln Ser Asp Ala Ser Glu Arg Cys Asp Asp Trp Gly Leu Asp Thr Met
            20                  25                  30

Arg Gln Ile Gln Val Phe Glu Asp Glu Pro Ala Arg Ile Lys Cys Pro
        35                  40                  45

Leu Phe Glu His Phe Leu Lys Phe Asn Tyr Ser Thr Ala His Ser Ala
    50                  55                  60

Gly Leu Thr Leu Ile Trp Tyr Trp Thr Arg Gln Asp Arg Asp Leu Glu

```
            65                  70                  75                  80
Glu Pro Ile Asn Phe Arg Leu Pro Glu Asn Arg Ile Ser Lys Glu Lys
                    85                  90                  95

Asp Val Leu Trp Phe Arg Pro Thr Leu Leu Asn Asp Thr Gly Asn Tyr
                    100                 105                 110

Thr Cys Met Leu Arg Asn Thr Thr Tyr Cys Ser Lys Val Ala Phe Pro
                    115                 120                 125

Leu Glu Val Val Gln Lys Asp Ser Cys Phe Asn Ser Pro Met Lys Leu
                    130                 135                 140

Pro Val His Lys Leu Tyr Ile Glu Tyr Gly Ile Gln Arg Ile Thr Cys
145                 150                 155                 160

Pro Asn Val Asp Gly Tyr Phe Pro Ser Ser Val Lys Pro Thr Ile Thr
                    165                 170                 175

Trp Tyr Met Gly Cys Tyr Lys Ile Gln Asn Phe Asn Asn Val Ile Pro
                    180                 185                 190

Glu Gly Met Asn Leu Ser Phe Leu Ile Ala Leu Ile Ser Asn Asn Gly
                    195                 200                 205

Asn Tyr Thr Cys Val Val Thr Tyr Pro Glu Asn Gly Arg Thr Phe His
                    210                 215                 220

Leu Thr Arg Thr Leu Thr Val Lys Val Val Gly Ser Pro Lys Asn Ala
225                 230                 235                 240

Val Pro Pro Val Ile His Ser Pro Asn Asp His Val Val Tyr Glu Lys
                    245                 250                 255

Glu Pro Gly Glu Glu Leu Leu Ile Pro Cys Thr Val Tyr Phe Ser Phe
                    260                 265                 270

Leu Met Asp Ser Arg Asn Glu Val Trp Trp Thr Ile Asp Gly Lys Lys
                    275                 280                 285

Pro Asp Asp Ile Thr Ile Asp Val Thr Ile Asn Glu Ser Ile Ser His
                    290                 295                 300

Ser Arg Thr Glu Asp Glu Thr Arg Thr Gln Ile Leu Ser Ile Lys Lys
305                 310                 315                 320

Val Thr Ser Glu Asp Leu Lys Arg Ser Tyr Val Cys His Ala Arg Ser
                    325                 330                 335

Ala Lys Gly Glu Val Ala Lys Ala Ala Lys Val Lys Gln Lys Val Pro
                    340                 345                 350

Ala Pro Arg Tyr Thr Val Gly Ser Gly Gly Asp Lys Thr His Thr
                    355                 360                 365

Cys Pro Pro Cys Pro Ala Pro Glu Leu Leu Gly Gly Pro Ser Val Phe
                    370                 375                 380

Leu Phe Pro Pro Lys Pro Lys Asp Thr Leu Met Ile Ser Arg Thr Pro
385                 390                 395                 400

Glu Val Thr Cys Val Val Val Asp Val Ser His Glu Asp Pro Glu Val
                    405                 410                 415

Lys Phe Asn Trp Tyr Val Asp Gly Val Glu Val His Asn Ala Lys Thr
                    420                 425                 430

Lys Pro Arg Glu Glu Gln Tyr Asn Ser Thr Tyr Arg Val Val Ser Val
                    435                 440                 445

Leu Thr Val Leu His Gln Asp Trp Leu Asn Gly Lys Glu Tyr Lys Cys
                    450                 455                 460

Lys Val Ser Asn Lys Ala Leu Pro Ala Pro Ile Glu Lys Thr Ile Ser
465                 470                 475                 480

Lys Ala Lys Gly Gln Pro Arg Glu Pro Gln Val Tyr Thr Leu Pro Pro
                    485                 490                 495
```

```
Cys Arg Asp Glu Leu Thr Lys Asn Gln Val Ser Leu Trp Cys Leu Val
            500                 505                 510

Lys Gly Phe Tyr Pro Ser Asp Ile Ala Val Glu Trp Glu Ser Asn Gly
        515                 520                 525

Gln Pro Glu Asn Asn Tyr Lys Thr Thr Pro Pro Val Leu Asp Ser Asp
    530                 535                 540

Gly Ser Phe Phe Leu Tyr Ser Ala Leu Thr Val Asp Lys Ser Arg Trp
545                 550                 555                 560

Gln Gln Gly Asn Val Phe Ser Cys Ser Val Met His Glu Ala Leu His
                565                 570                 575

Asn His Tyr Thr Gln Lys Ser Leu Ser Leu Ser Pro Gly Lys
            580                 585                 590

<210> SEQ ID NO 6
<211> LENGTH: 1770
<212> TYPE: DNA
<213> ORGANISM: Homo sapiens

<400> SEQUENCE: 6
atgactctgc tgtggtgcgt cgtgtccctc tacttctacg gcatcctcca gtccgacgcc      60
agcgagaggt gcgatgactg gggcctggac accatgaggc agatccaggt gtttgaggac     120
gagcctgcca ggattaagtg ccccctcttc gagcactttc tgaagttcaa ctacagcacc     180
gctcacagcg ctggcctgac actgatctgg tactggacaa ggcaggacag ggatctcgag     240
gagcccatca acttcaggct gcccgaaaac agaatcagca aggagaagga cgtgctgtgg     300
ttcagaccca ccctcctcaa cgacacaggc aactacacct gcatgctcag gaacaccacc     360
tactgcagca aggtggcctt ccctctcgag gtggtccaga aggacagctg cttcaacagc     420
cccatgaagc tgcccgtcca taaactgtac atcgagtacg catccagag gatcacatgc     480 cccaacgtgg acggctactt ccccagctcc gtgaagccca ccatcacatg gtacatgggc     540
tgttacaaaa tccagaactt taacaacgtc atccccgagg gcatgaatct gtccttcctg     600
atcgccctga tcagcaacaa cggcaattac acctgcgtcg tgacctaccc cgaaaacggc     660
aggaccttcc acctgaccag gaccctgacc gtgaaagtcg tgggaagccc caagaatgcc     720 gtgcccccg tgatccattc ccccaacgac cacgtggtgt acgagaagga gcctggagag     780
gagctgctga tccctgcac agtgtactc tccttcctga tggactccag gaatgaagtg     840
tggtggacca tcgacggcaa gaagcctgac gacatcacca tcgatgtgac catcaacgag     900
agcatcagcc acagcaggac cgaggacgag accaggaccc agatcctgag catcaagaaa     960
gtcaccagcg aggacctcaa gagaagctac gtctgtcacg ccagaagcgc caaggcgag    1020 gtggccaagg ctgctaaggt gaaacagaaa gtgcccgctc ctaggtacac agtcggatcc    1080
ggtggaggtg acaaaactca cacatgccca ccgtgcccag ctccggaact cctgggcgga    1140
ccgtcagtct tcctcttccc cccaaaaccc aaggacaccc tcatgatctc ccggaccct    1200 gaggtcacat gcgtggtggt ggacgtgagc cacgaagacc ctgaggtcaa gttcaactgg    1260
tacgtggacg gcgtggaggt gcataatgcc aagacaaagc cgcgggagga gcagtacaac    1320
agcacgtacc gtgtggtcag cgtcctcacc gtcctgcacc aggactggct gaatggcaag    1380
gagtacaagt gcaaggtctc caacaaagcc ctcccagccc ccatcgagaa aaccatctcc    1440
aaagccaaag gcagccccg agaaccacag gtgtacaccc tgcccccatg tcgggatgag    1500
ctgaccaaga accaggtcag cctgtggtgc ctggtcaaag gcttctatcc cagcgacatc    1560
```

```
gccgtggagt gggagagcaa tgggcagccg agaacaact  acaagaccac gcctcccgtg    1620
ttggactccg acggctcctt cttcctctac agcgcgctca ccgtggacaa gagcaggtgg    1680 cagcaggga  acgtcttctc atgctccgtg atgcatgagg ctctgcacaa ccactacacg    1740
cagaagagcc tctccctgtc tccgggtaaa                                    1770

<210> SEQ ID NO 7
<211> LENGTH: 12816
<212> TYPE: DNA
<213> ORGANISM: Homo sapiens

<400> SEQUENCE: 7
agcttgccac catgaaggtc ctgctcaggc tgatctgctt cattgccctg ctcatcagca      60
gcctggaagc cgacaagtgc aaggagaggg aggagaagat catcctcgtc agctccgcca     120
acgagattga tgtcaggccc tgcccccctca accccaatga gcacaagggc acaatcacct    180
ggtacaagga cgacagcaag acccctgtct ccaccgagca ggccagcaga atccaccagc     240
acaaagagaa gctgtggttc gtgcctgcca aggtggaaga cagcggccac tactactgtg     300
tggtgaggaa cagctcctac tgcctcagga tcaagatctc cgccaagttc gtggagaacg     360
agcccaacct ctgttacaac gctcaggcta ttttcaagca aaagtccccc gtggctggag     420
acggaggcct ggtctgtccc tacatggagt tcttcaagaa tgagaataat gagctcccca     480
agctccagtg gtacaaggac tgtaagcctc tgctcctgga caacatccac ttctccggcg     540
tgaaggacag actgatcgtc atgaacgtgg ccgagaagca gggggaaac tacacctgtc      600 acgcctccta cacctacctc ggcaagcaat atcccatcac cagggtcatc gagttcatca     660
ccctcgaaga gaacaagccc acaaggcctg tcatcgtcag ccccgccaat gaaaccatgg     720
aggtggacct cggcagccag atccagctga tctgcaacgt gacaggccag ctcagcgaca     780
ttgcctactg gaagtggaac ggctccgtga tcgacgaaga tgatcccgtg ctgggcgagg     840
actactatag cgtggagaac cccgccaaca aagaaggag  caccctgatc accgtgctga     900
acatcagcga gatcgagtcc agattctata gcatcctttt cacctgcttt gccaagaaca     960
cccacggcat cgacgccgct tacatccagc tgatctatcc cgtgaccaac ggatccggtg    1020
gaggtgacaa aactcacaca tgcccaccgt gcccagctcc ggaactcctg gcggaccgt     1080 cagtcttcct cttcccccca aaacccaagg acaccctcat gatctcccgg acccctgagg    1140
tcacatgcgt ggtggtggac gtgagccacg aagaccctga ggtcaagttc aactggtacg    1200
tggacggcgt ggaggtgcat aatgccaaga caaagccgcg ggaggagcag tacaacagca    1260
cgtaccgtgt ggtcagcgtc ctcaccgtcc tgcaccagga ctggctgaat ggcaaggagt    1320
acaagtgcaa ggtctccaac aaagccctcc cagcccccat cgagaaaacc atctccaaag    1380
ccaaagggca gccccgagaa ccacaggtgt gtaccctgcc cccatcccgg gatgagctga    1440
ccaagaacca ggtcagcctg agttgcgcgg tcaaaggctt ctatcccagc gacatcgccg    1500
tggagtggga gagcaatggg cagccggaga caactacaa  gaccacgcct cccgtgttgg    1560
actccgacgg ctccttcaag ctcgtcagca agctcaccgt ggacaagagc aggtggcagc    1620
aggggaacgt cttctcatgc tccgtgatgc atgaggctct gcacaaccac tacacgcaga    1680
agagcctctc cctgtctccg ggtaaataat agaattcatt gatcataatc agccatacca    1740
catttgtaga ggttttactt gctttaaaaa acctcccaca cctccccctg aacctgaaac    1800
ataaaatgaa tgcaattgtt gttgttaact tgtttattgc agcttataat ggttacaaat    1860
aaagcaatag catcacaaat ttcacaaata aagcattttt ttcactgcat tctagttgtg    1920
```

```
gtttgtccaa actcatcaat gtatcttatc atgtctggcg ccgccgata tttgaaaata    1980 tggcatattg aaaatgtcgc cgatgtgagt ttctgtgtaa ctgatatcgc cattttttcca   2040 aaagtgattt ttgggcatac gcgatatctg gcgatagcgc ttatatcgtt tacgggggat    2100
ggcgatagac gactttggtg acttgggcga ttctgtgtgt cgcaaatatc gcagtttcga    2160
tataggtgac agacgatatg aggctatatc gccgatagag gcgacatcaa gctggcacat    2220
ggccaatgca tatcgatcta tacattgaat caatattggc cattagccat attattcatt    2280
ggttatatag cataaatcaa tattggctat tggccattgc atacgttgta tccatatcat    2340
aatatgtaca tttatattgg ctcatgtcca acattaccgc catgttgaca ttgattattg    2400
actagttatt aatagtaatc aattacgggg tcattagttc atagcccata tatggagttc    2460
cgcgttacat aacttacggt aaatggcccg cctggctgac cgcccaacga cccccgccca    2520
ttgacgtcaa taatgacgta tgttcccata gtaacgccaa tagggacttt ccattgacgt    2580
caatgggtgg agtatttacg gtaaactgcc cacttggcag tacatcaagt gtatcatatg    2640
ccaagtacgc cccctattga cgtcaatgac ggtaaatggc ccgcctggca ttatgcccag    2700
tacatgacct tatgggactt tcctacttgg cagtacatct acgtattagt catcgctatt    2760
accatggtga tgcggttttg gcagtacatc aatgggcgtg gatagcggtt tgactcacgg    2820
ggatttccaa gtctccaccc cattgacgtc aatgggagtt tgttttggca ccaaaatcaa    2880
cgggactttc caaaatgtcg taacaactcc gccccattga cgcaaatggg cggtaggcgt    2940
gtacggtggg aggtctatat aagcagagct cgtttagtga accgtcagat cgcctggaga    3000
cgccatccac gctgttttga cctccataga agacaccggg accgatccag cctccgcggc    3060
cgggaacggt gcattggaac gcggattccc cgtgccaaga gtgacgtaag taccgcctat    3120
agagtctata ggcccacccc cttggcttct tatgcatgct atactgtttt tggcttgggg    3180
tctatacacc cccgcttcct catgttatag gtgatggtat agcttagcct ataggtgtgg    3240
gttattgacc attattgacc actcccctat tggtgacgat actttccatt actaatccat    3300
aacatggctc tttgccacaa ctctctttat tggctatatg ccaatacact gtccttcaga    3360
gactgacacg gactctgtat ttttacagga tggggtctca tttattattt acaaattcac    3420
atatacaaca ccaccgtccc cagtgcccgc agttttatt aaacataacg tgggatctcc    3480
acgcgaatct cgggtacgtg ttccggacat gggctcttct ccggtagcgg cggagcttct    3540
acatccgagc cctgctccca tgcctccagc gactcatggt cgctcggcag ctccttgctc    3600
ctaacagtgg aggccagact taggcacagc acgatgccca ccaccaccag tgtgccgcac    3660
aaggccgtgg cggtagggta tgtgtctgaa aatgagctcg gggagcgggc ttgcaccgct    3720
gacgcatttg gaagacttaa ggcagcggca gaagaagatg caggcagctg agttgttgtg    3780
ttctgataag agtcagaggt aactcccgtt gcggtgctgt taacggtgga gggcagtgta    3840
gtctgagcag tactcgttgc tgccgcgcgc gccaccagac ataatagctg acagactaac    3900
agactgttcc tttccatggg tctttttctgc agtcaccgtc cttgacacga agcttgccac    3960
catgactctg ctgtggtgcg tcgtgtccct ctacttctac ggcatcctcc agtccgacgc    4020
cagcgagagg tgcgatgact gggggcctgga caccatgagg cagatccagg tgtttgagga    4080
cgagcctgcc aggattaagt gccccctctt cgagcacttt ctgaagttca actacagcac    4140
cgctcacagc gctggcctga cactgatctg gtactggaca aggcaggaca gggatctcga    4200
ggagcccatc aacttcaggc tgcccgaaaa cagaatcagc aaggagaagg acgtgctgtg    4260
```

```
gttcagaccc accctcctca acgacacagg caactacacc tgcatgctca ggaacaccac    4320
ctactgcagc aaggtggcct tccctctcga ggtggtccag aaggacagct gcttcaacag    4380
ccccatgaag ctgcccgtcc ataaactgta catcgagtac ggcatccaga ggatcacatg    4440
ccccaacgtg gacggctact cccccagctc cgtgaagccc accatcacat ggtacatggg    4500
ctgttacaaa atccagaact ttaacaacgt catccccgag ggcatgaatc tgtccttcct    4560
gatcgccctg atcagcaaca acggcaatta cacctgcgtc gtgacctacc ccgaaaacgg    4620
caggaccttc cacctgacca ggaccctgac cgtgaaagtc gtgggaagcc ccaagaatgc    4680 cgtgccccccc gtgatccatt cccccaacga ccacgtggtg tacgagaagg agcctggaga    4740
ggagctgctg atcccctgca cagtgtactt ctccttcctg atggactcca ggaatgaagt    4800
gtggtggacc atcgacggca agaagcctga cgacatcacc atcgatgtga ccatcaacga    4860
gagcatcagc cacagcagga ccgaggacga gaccaggacc cagatcctga gcatcaagaa    4920
agtcaccagc gaggacctca agagaagcta cgtctgtcac gccagaagcg ccaaggcga    4980 ggtggccaag gctgctaagg tgaaacagaa agtgcccgct cctaggtaca cagtcggatc    5040
cggtggaggt gacaaaactc acacatgccc accgtgccca gctccggaac tcctgggcgg    5100
accgtcagtc ttcctcttcc ccccaaaacc caaggacacc ctcatgatct cccggacccc    5160
tgaggtcaca tgcgtggtgg tggacgtgag ccacgaagac cctgaggtca agttcaactg    5220
gtacgtggac ggcgtggagg tgcataatgc caagacaaag ccgcgggagg agcagtacaa    5280
cagcacgtac cgtgtggtca gcgtcctcac cgtcctgcac caggactggc tgaatggcaa    5340
ggagtacaag tgcaaggtct ccaacaaagc cctcccagcc cccatcgaga aaaccatctc    5400
caaagccaaa gggcagcccc gagaaccaca ggtgtacacc ctgcccccat gtcgggatga    5460
gctgaccaag aaccaggtca gcctgtggtg cctggtcaaa ggcttctatc ccagcgacat    5520
cgccgtggag tgggagagca atgggcagcc ggagaacaac tacaagacca cgcctcccgt    5580
gttggactcc gacggctcct tcttcctcta cagcgcgctc accgtggaca agagcaggtg    5640
gcagcagggg aacgtcttct catgctccgt gatgcatgag gctctgcaca accactacac    5700
gcagaagagc ctctccctgt ctccgggtaa ataatagaat tcattgatca taatcagcca    5760
taccacattt gtagaggttt tacttgcttt aaaaaacctc ccacacctcc ccctgaacct    5820
gaaacataaa atgaatgcaa ttgttgttgt taacttgttt attgcagctt ataatggtta    5880
caaataaagc aatagcatca caaatttcac aaataaagca tttttttcac tgcattctag    5940
ttgtggtttg tccaaactca tcaatgtatc ttatcatgtc tggatcctct acgccggacg    6000
catcgtggcc ggcatcaccg gcgccacagg tgcggttgct ggcgcctata tcgccgacat    6060
caccgatggg gaagatcggg ctcgccactt cgggctcatg agcgcttgtt tcggcgtggg    6120
tatggtggca ggccccgtgg ccgggggact gttgggcgcc atctccttgc atgcaccatt    6180
ccttgcggcg gcggtgctca acggcctcaa cctactactg ggctgcttcc taatgcagga    6240
gtcgcataag ggagagcgtc gaccgcggc cgcgttgctg gcgttttcc ataggctccg    6300 ccccccctgac gagcatcaca aaaatcgacg ctcaagtcag aggtggcgaa acccgacagg    6360
actataaaga taccaggcgt ttccccctgg aagctccctc gtgcgctctc ctgttccgac    6420
cctgccgctt accggatacc tgtccgcctt tctcccttcg ggaagcgtgg cgctttctca    6480
tagctcacgc tgtaggtatc tcagttcggt gtaggtcgtt cgctccaagc tgggctgtgt    6540
gcacgaaccc cccgttcagc ccgaccgctg cgccttatcc ggtaactatc gtcttgagtc    6600
caacccggta agacacgact tatcgccact ggcagcagcc actggtaaca ggattagcag    6660
```

```
agcgaggtat gtaggcggtg ctacagagtt cttgaagtgg tggcctaact acggctacac    6720
tagaagaaca gtatttggta tctgcgctct gctgaagcca gttaccttcg gaaaaagagt    6780
tggtagctct tgatccggca aacaaaccac cgctggtagc ggtggttttt ttgtttgcaa    6840
gcagcagatt acgcgcagaa aaaaggatc tcaagaagat cctttgatct tttctacggg    6900
gtctgacgct cagtggaacg aaaactcacg ttaagggatt ttggtcatga gattatcaaa    6960
aaggatcttc acctagatcc ttttaaatta aaaatgaagt tttaaatcaa tctaaagtat    7020
atatgagtaa acttggtctg acagttacca atgcttaatc agtgaggcac ctatctcagc    7080
gatctgtcta tttcgttcat ccatagttgc ctgactcccc gtcgtgtaga taactacgat    7140
acgggagggc ttaccatctg gccccagtgc tgcaatgata ccgcgagacc cacgctcacc    7200
ggctccagat ttatcagcaa taaaccagcc agccggaagg gccgagcgca gaagtggtcc    7260
tgcaacttta tccgcctcca tccagtctat taattgttgc cgggaagcta gagtaagtag    7320
ttcgccagtt aatagtttgc gcaacgttgt tgccattgct acaggcatcg tggtgtcacg    7380
ctcgtcgttt ggtatggctt cattcagctc cggttcccaa cgatcaaggc gagttacatg    7440
atcccccatg ttgtgcaaaa aagcggttag ctccttcggt cctccgatcg ttgtcagaag    7500
taagttggcc gcagtgttat cactcatggt tatggcagca ctgcataatt ctcttactgt    7560
catgccatcc gtaagatgct tttctgtgac tggtgagtac tcaaccaagt cattctgaga    7620
atagtgtatg cggcgaccga gttgctcttg cccggcgtca atacgggata ataccgcgcc    7680
acatagcaga actttaaaag tgctcatcat tggaaaacgt tcttcggggc gaaaactctc    7740
aaggatctta ccgctgttga tccagttcga tgtaaccc actcgtgcac ccaactgatc    7800
ttcagcatct tttactttca ccagcgtttc tgggtgagca aaaacaggaa ggcaaaatgc    7860
cgcaaaaaag ggaataaggg cgacacggaa atgttgaata ctcatactct ccttttttca    7920
atattattga agcatttatc agggttattg tctcatgagc ggatacatat ttgaatgtat    7980
ttagaaaaat aaacaaatag gggttccgcg cacatttccc cgaaaagtgc cacctgacgt    8040
ctaagaaacc attattatca tgacattaac ctataaaaat aggcgtatca cgaggccctg    8100
atggctcttt gcggcaccca tcgttcgtaa tgttccgtgg caccgaggac aaccctcaag    8160
agaaaatgta atcacactgg ctcaccttcg ggtgggcctt tctgcgttta taggagaca    8220 cttatgtttt aagaaggttg gtaaattcct tgcggctttg gcagccaagc tagatccggc    8280
tgtggaatgt gtgtcagtta gggtgtggaa agtccccagg ctccccagca ggcagaagta    8340
tgcaaagcat gcatctcaat tagtcagcaa ccaggtgtgg aaagtcccca ggctccccag    8400
caggcagaag tatgcaaagc atgcatctca attagtcagc aaccatagtc cgcccctaa    8460 ctccgcccat cccgccccta actccgccca gttccgccca ttctccgccc catggctgac    8520 taatttttt tatttatgca gaggccgagg ccgcctcggc ctctgagcta ttccagaagt    8580
agtgaggagg cttttttgga ggcctaggct tttgcaaaaa gctagcttgg ggccaccgct    8640
cagagcacct tccaccatgg ccacctcagc aagttccac ttgaacaaaa acatcaagca    8700
aatgtacttg tgcctgcccc agggtgagaa agtccaagcc atgtatatct gggttgatgg    8760
tactggagaa ggactgcgct gcaaaacccg caccctggac tgtgagccca gtgtgtaga    8820 agagttacct gagtggaatt ttgatggctc tagtaccttt cagtctgagg ctccaacag    8880 tgacatgtat ctcagccctg ttgccatgtt tcgggacccc ttccgcagag atcccaacaa    8940
gctggtgttc tgtgaagttt tcaagtacaa ccggaagcct gcagagacca atttaaggca    9000
```

```
ctcgtgtaaa cggataatgg acatggtgag caaccagcac ccctggtttg gaatggaaca      9060
ggagtatact ctgatgggaa cagatgggca ccctttggt tggccttcca atggctttcc       9120
tgggccccaa ggtccgtatt actgtggtgt gggcgcagac aaagcctatg gcagggatat      9180
cgtggaggct cactaccgcg cctgcttgta tgctggggtc aagattacag gaacaaatgc      9240
tgaggtcatg cctgcccagt gggaactcca aataggaccc tgtgaaggaa tccgcatggg      9300
agatcatctc tgggtggccc gtttcatctt gcatcgagta tgtgaagact ttggggtaat      9360
agcaaccttt gaccccaagc ccattcctgg gaactggaat ggtgcaggct gccataccaa      9420
ctttagcacc aaggccatgc gggaggagaa tggtctgaag cacatcgagg aggccatcga      9480
gaaactaagc aagcggcacc ggtaccacat tcgagcctac gatcccaagg ggggcctgga      9540
caatgcccgt ggtctgactg ggttccacga aacgtccaac atcaacgact tttctgctgg      9600
tgtcgccaat cgcagtgcca gcatccgcat tccccggact gtcggccagg agaagaaagg      9660
ttactttgaa gaccgcggcc cctctgccaa ttgtgacccc tttgcagtga cagaagccat      9720
cgtccgcaca tgccttctca tgagactgg cgacgagccc ttccaataca aaaactaatt       9780
agactttgag tgatcttgag cctttcctag ttcatcccac cccgcccag agagatcttt        9840
gtgaaggaac cttacttctg tggtgtgaca taattggaca aactacctac agagatttaa      9900
agctctaagg taaatataaa atttttaagt gtataatgtg ttaaactact gattctaatt      9960
gtttgtgtat tttagattcc aacctatgga actgatgaat gggagcagtg gtggaatgcc     10020
tttaatgagg aaaacctgtt ttgctcagaa gaaatgccat ctagtgatga tgaggctact     10080
gctgactctc aacattctac tcctccaaaa aagaagagaa aggtagaaga ccccaaggac     10140
ttccttcag aattgctaag ttttttgagt catgctgtgt ttagtaatag aactcttgct      10200
tgctttgcta tttacaccac aaaggaaaaa gctgcactgc tatacaagaa aattatgaa      10260
aaatattctg taacctttat aagtaggcat aacagttata atcataacat actgtttttt     10320
cttactccac acaggcatag agtgtctgct attaataact atgctcaaaa attgtgtacc     10380
tttagctttt taatttgtaa aggggttaat aaggaatatt tgatgtatag tgccttgact     10440
agagatcata atcagccata ccacatttgt agaggtttta cttgctttaa aaaacctccc     10500
acacctcccc ctgaacctga aacataaaat gaatgcaatt gttgttgtta acttgtttat     10560
tgcagcttat aatggttaca aataaagcaa tagcatcaca aatttcacaa ataaagcatt     10620
ttttcactg cattctagtt gtggtttgtc caaactcatc aatgtatctt atcatgtctg      10680
gatctagctt cgtgtcaagg acggtgactg cagtgaataa taaaatgtgt gtttgtccga     10740
aatacgcgtt ttgagatttc tgtcgccgac taaattcatg tcgcgcgata gtggtgttta     10800
tcgccgatag agatggcgat attggaaaaa tcgatatttg aaaatatggc atattgaaaa     10860
tgtcgccgat gtgagtttct gtgtaactga tatcgccatt tttccaaaag tgattttgg      10920
gcatacgcga tatctggcga tagcgcttat atcgtttacg ggggatggcg atagacgact     10980
ttggtgactt gggcgattct gtgtgtcgca aatatcgcag tttcgatata ggtgacagac     11040
gatatgaggc tatatcgccg atagaggcga catcaagctg gcacatggcc aatgcatatc     11100
gatctataca ttgaatcaat attggccatt agccatatta ttcattggtt atatagcata     11160
aatcaatatt ggctattggc cattgcatac gttgtatcca tatcataata tgtacattta     11220
tattggctca tgtccaacat taccgccatg ttgacattga ttattgacta gttattaata     11280
gtaatcaatt acgggtcat tagttcatag cccatatatg gagttccgcg ttacataact      11340
tacggtaaat ggcccgcctg gctgaccgcc caacgacccc cgcccattga cgtcaataat     11400
```

```
gacgtatgtt cccatagtaa cgccaatagg gactttccat tgacgtcaat gggtggagta    11460
tttacggtaa actgcccact tggcagtaca tcaagtgtat catatgccaa gtacgccccc    11520
tattgacgtc aatgacggta aatggcccgc ctggcattat gcccagtaca tgaccttatg    11580
ggactttcct acttggcagt acatctacgt attagtcatc gctattacca tggtgatgcg    11640
gttttggcag tacatcaatg ggcgtggata gcggtttgac tcacggggat ttccaagtct    11700
ccaccccatt gacgtcaatg ggagtttgtt ttggcaccaa aatcaacggg actttccaaa    11760
atgtcgtaac aactccgccc cattgacgca aatgggcggt aggcgtgtac ggtgggaggt    11820
ctatataagc agagctcgtt tagtgaaccg tcagatcgcc tggagacgcc atccacgctg    11880
ttttgacctc catagaagac accgggaccg atccagcctc cgcggccggg aacggtgcat    11940
tggaacgcgg attccccgtg ccaagagtga cgtaagtacc gcctatagag tctataggcc    12000
cacccccttg gcttcttatg catgctatac tgttttggc ttggggtcta tacacccccg    12060
cttcctcatg ttataggtga tggtatagct tagcctatag gtgtgggtta ttgaccatta    12120
ttgaccactc ccctattggt gacgatactt tccattacta atccataaca tggctctttg    12180
ccacaactct ctttattggc tatatgccaa tacactgtcc ttcagagact gacacggact    12240
ctgtattttt acaggatggg gtctcattta ttatttacaa attcacatat acaacaccac    12300
cgtccccagt gcccgcagtt tttattaaac ataacgtggg atctccacgc gaatctcggg    12360
tacgtgttcc ggacatgggc tcttctccgg tagcggcgga gcttctacat ccgagccctg    12420
ctcccatgcc tccagcgact catggtcgct cggcagctcc ttgctcctaa cagtggaggc    12480
cagacttagg cacagcacga tgcccaccac caccagtgtg ccgcacaagg ccgtggcggt    12540
agggtatgtg tctgaaaatg agctcgggga gcgggcttgc accgctgacg catttggaag    12600
acttaaggca gcggcagaag aagatgcagg cagctgagtt gttgtgttct gataagagtc    12660
agaggtaact cccgttgcgg tgctgttaac ggtggagggc agtgtagtct gagcagtact    12720
cgttgctgcc gcgcgcgcca ccagacataa tagctgacag actaacagac tgttcctttc    12780
catgggtctt ttctgcagtc accgtccttg acacga                              12816
```